United States Patent

Tanikawa et al.

[11] Patent Number: 6,114,369
[45] Date of Patent: Sep. 5, 2000

[54] BENZIMIDAZOLE COMPOUND

[75] Inventors: Keizo Tanikawa; Yoshimasa Kamikawaji; Mitsuaki Hirotsuka, all of Funabashi; Takehisa Iwama, Minamisaitama-gun; Akiko Yamamoto, Minamisaitama-gun; Yoichiro Fujita, Minamisaitama-gun, all of Japan

[73] Assignee: Nissan Chemical Industries, Ltd., Tokyo, Japan

[21] Appl. No.: 09/403,763

[22] PCT Filed: Apr. 30, 1998

[86] PCT No.: PCT/JP98/01986

§ 371 Date: Nov. 1, 1999

§ 102(e) Date: Nov. 1, 1999

[87] PCT Pub. No.: WO98/50368

PCT Pub. Date: Nov. 12, 1998

[30] Foreign Application Priority Data

May 1, 1997 [JP] Japan ................................. 9-113723
Mar. 6, 1998 [JP] Japan ................................. 10-55303

[51] Int. Cl.[7] .................. A61K 31/4184; C07D 235/14; C07D 235/30
[52] U.S. Cl. .................. 514/394; 548/307.4; 548/309.7
[58] Field of Search .............. 548/307.4, 309.7; 514/394

[56] References Cited

U.S. PATENT DOCUMENTS 5,290,801 3/1994 Higley et al. ....................... 514/394

Primary Examiner—Laura L. Stockton
Attorney, Agent, or Firm—Oblon, Spivak, McClelland, Maier & Neustadt, P.C.

[57] ABSTRACT

A benzimidazole derivative of the formula (I) or its salt:

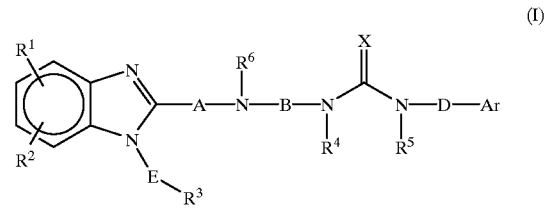

wherein A is a single bond or a $C_{1-2}$ alkylene group (this alkylene group may optionally be substituted by a $C_{1-4}$ alkyl group), $R^6$ is a $C_{1-4}$ alkyl group (this alkyl group may optionally be substituted by a phenyl group), B is a $C_{2-3}$ alkylene group (this alkylene group may optionally be substituted by a $C_{1-4}$ alkyl group), X is an oxygen atom, a sulfur atom or $NR^7$ (wherein $R^7$ is a nitro group, a cyano group or a $C_{1-4}$ alkoxy group), each of $R^1$ and $R^2$ which are independent of each other, is a hydrogen atom, a halogen atom, a $C_{1-4}$ alkyl group or a $C_{1-4}$ alkoxy group, E is a $C_{1-2}$ alkylene group (this alkylene group may optionally be substituted by a $C_{1-4}$ alkyl group), $R^3$ is a phenyl group (this phenyl group may optionally be substituted by a halogen atom, a $C_{1-4}$ alkyl group or a $C_{1-4}$ alkoxy group), a $C_{1-4}$ alkoxy group or a benzyloxy group, each of $R^4$ and $R^5$ which are independent of each other, is a $C_{1-4}$ alkyl group (this alkyl group may optionally be substituted by a phenyl group), D is a $C_{1-2}$ alkylene group (this alkylene group may optionally be substituted by a $C_{1-4}$ alkyl group), and Ar is a phenyl group.

10 Claims, No Drawings

BENZIMIDAZOLE COMPOUND

This application is a 371 of PCT/JP98/01986 filed Apr. 30, 1998.

BACKGROUND OF THE INVENTION

The present invention relates to a novel benzimidazole derivative having an antiallergic activity and a drug containing it as an active ingredient.

DESCRIPTION OF THE BACKGROUND

In the treatment of type I allergy-related diseases such as pollinosis, urticaria, atopic dermatitis, allergic rhinitis and asthma, antihistamines and steroids have heretofore been frequently used. However, problems still remain with respect to the clinical usefulness thereof. The above mentioned allergy-related diseases are triggered by an immune reaction of a specific antigen with IgE antibody and progress to a chronic state via inflammation of the diseased portion or tissue damage. It has been suggested that during this process, various chemical mediators are mutually closely related to the pathologic progress. Among them, histamine is believed to be involved mainly at the initial stage of the pathologic progress from the characteristics of its pharmacological action. This is considered to be the reason why a problem remains with respect to the clinical usefulness of antihistamines. On the other hand, steroids which are used primarily in severe cases, show pharmacological activities to inhibit a series of processes of immuno-inflammatory responses in various fashions and are believed to exhibit a high level of effectiveness. However, steroids have a problem of severe side effects, and there are many restrictions in their application to oral administration or repeated administration. Thus, in the field of treatment of type I allergy-related diseases, it is very much desired to develop a drug having a new mechanism for action and having a high level of effectiveness.

In recent years, it has been reported that substance P which is a neuropeptide, acts as a mediator to promote allergic symptoms and is deeply concerned in the inflammatory symptoms particularly in the chronic phase, (TIPS, 81, 24 (1987); Am. J. Respir. Crit. Care Med., 151, 613 (1995); J. Allergy Clin. Immunol., 92, 95 (1993)). Therefore, an antagonist of substance P is considered to be capable of effectively curing the allergic symptoms in the chronic phase (particularly the chronic inflammation).

Substance P is a member of the neurokinin family, and it is known that it is widely concerned in activation of macrophages or lymphocytes, and in immunity and inflammation as a regulatory factor for production of cytokine (IL1, TNF, IL6), and it causes inflammatory symptoms such as increase in vascular permeability, plasma leakage and secretory gland stimulation. Further, it functions as a transmitter of pain from peripheral to central, and it controls the transmission system of dopamine and adrenaline in brain.

Accordingly, a substance P antagonist is considered to be effective not only as an antiallergic agent but also as analgesics or psychomimetics.

Further, a drug having not only substance P antagonistic activities but also antihistamine activities, is considered to be effective for treatment of a wide range of allergic symptoms ranging from acute phase to chronic phase and thus is expected to be a drug which has clinically high curing effects.

SUMMARY OF THE INVENTION

As a result of extensive studies, the present inventors have found that the benzimidazole derivatives of the present invention have substance P antagonistic activities, and further that among the compounds of the present invention, many also have antihistamine activities.

DETAILED DESCRIPTION OF THE PREFERRED EMBODIMENTS

Benzimidazoles having antihistamine activities have already been disclosed in e.g. JP-A-59-199679, JP-A-58-79983, EP-232937B, EP144101B and U.S. Pat. No. 4,219,559. However, the compounds of the present invention are not included in such disclosed benzimidazoles. Further, such prior art references disclose nothing about substance P antagonistic activities.

Thus, it has been found that the compounds of the present invention are superior compounds as antiallergic agents, and they are not only useful as active ingredients for preventive or curing agents for pollinosis, urticaria, atopic dermatitis, allergic rhinitis and asthma etc., but also effective against other substance P related diseases, for example, eye diseases such as conjunctivitis and spring catarrh; inflammatory diseases such as chronic rheumatoid arthritis; pains such as migraine, headache, toothache and aches accompanying various diseases; gastrointestinal diseases such as ulcerative colitis and Crohn's disease; and mental diseases such as depression and dysthymia. The present invention has been accomplished on the basis of these discoveries.

The present invention provides a benzimidazole derivative of the formula (I) or its salt:

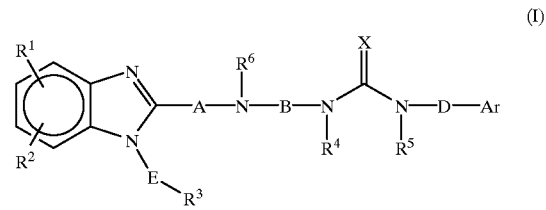

(I)

wherein A is a single bond or a $C_{1-2}$ alkylene group (this alkylene group may optionally be substituted by a $C_{1-4}$ alkyl group), $R^6$ is a $C_{1-4}$ alkyl group (this alkyl group may optionally be substituted by a phenyl group), B is a $C_{2-3}$ alkylene group (this alkylene group may optionally be substituted by a $C_{1-4}$ alkyl group), X is an oxygen atom, a sulfur atom or $NR^7$ (wherein $R^7$ is a nitro group, a cyano group or a $C_{1-4}$ alkoxy group), each of $R^1$ and $R^2$ which are independent of each other, is a hydrogen atom, a halogen atom, a $C_{1-4}$ alkyl group or a $C_{1-4}$ alkoxy group, E is a $C_{1-2}$ alkylene group (this alkylene group may optionally be substituted by a $C_{1-4}$ alkyl group), $R^3$ is a phenyl group (this phenyl group may optionally be substituted by a halogen atom, a $C_{1-4}$ alkyl group or a $C_{1-4}$ alkoxy group), a $C_{1-4}$ alkoxy group or a benzyloxy group, each of $R^4$ and $R^5$ which are independent of each other, is a $C_{1-4}$ alkyl group (this alkyl group may optionally be substituted by a phenyl group), D is a $C_{1-2}$ alkylene group (this alkylene group may optionally be substituted by a $C_{1-4}$ alkyl group), and Ar is a phenyl group (this phenyl group may optionally be substituted by a halogen atom, a $C_{1-4}$ alkyl group, a $C_{1-4}$ alkoxy group or a trifluoromethyl group), a process for its production and a pharmaceutical composition containing it as an active ingredient.

Now, the substituents relating to the compound of the present invention will be described.

In this specification, n means normal, i iso, s secondary, t tertiary, c cyclo, Me methyl, Et ethyl, Bu butyl, Ph phenyl, and Bn benzyl.

The $C_{1-2}$ alkylene group includes methylene and ethylene.

The $C_{2-3}$ alkylene group includes ethylene and trimethylene.

The $C_{1-4}$ alkyl group may be linear, branched or cyclic and includes methyl, ethyl, n-propyl, i-propyl, c-propyl, n-butyl, i-butyl, s-butyl, t-butyl and c-butyl.

The $C_{1-4}$ alkoxy group may be linear, branched or cyclic and includes methoxy, ethoxy, n-propoxy, i-propoxy, c-propoxy, n-butoxy, i-butoxy, s-butoxy, t-butoxy and c-butoxy.

The halogen atom includes fluorine, chlorine, bromine and iodine.

Now, A, B, D, E, Ar, X, $R^1$, $R^2$, $R^3$, $R^4$, $R^5$ and $R^6$ in the compound (I) of the present invention will be described in detail.

Specific examples of A include a single bond, $CH_2$, CHMe, $CH_2CH_2$ and $CH_2$CHMe, preferably a single bond and $CH_2$.

Specific examples of B include $CH_2CH_2$, $CH_2$CHMe, CHMeCH$_2$, CHMeCHMe, $CH_2CH_2CH_2$, CHMeCH$_2$CH$_2$, $CH_2$CHMeCH$_2$, $CH_2CH_2$CHMe, CHMeCHMeCH$_2$, CHMeCH$_2$CHMe, $CH_2$CHMeCHMe and CHMeCHMeCHMe, preferably $CH_2CH_2$ and $CH_2CH_2CH_2$.

Specific examples of D include $CH_2$, CHMe, $CH_2CH_2$ and $CH_2$CHMe, preferably $CH_2$, CHMe and $CH_2CH_2$.

Specific examples of E include $CH_2$, CHMe, $CH_2CH_2$ and $CH_2$CHMe, preferably $CH_2$ and $CH_2CH_2$.

Specific examples of Ar include phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2-trifluoromethylphenyl, 3-trifluoromethylphenyl, 4-trifluoromethylphenyl, 2-methylphenyl, 3-methylphenyl, 4-methylphenyl, 2-methoxyphenyl, 3-methoxyphenyl, 4-methoxyphenyl, 2,3-difluorophenyl, 2,4-difluorophenyl, 2,5-difluorophenyl, 2,6-difluorophenyl, 3,4-difluorophenyl, 3,5-difluorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,3-dibromophenyl, 2,4-dibromophenyl, 2,5-dibromophenyl, 2,6-dibromophenyl, 3,4-dibromophenyl, 3,5-dibromophenyl, 2,3-diiodophenyl, 2,4-diiodophenyl, 2,5-diiodophenyl, 2,6-diiodophenyl, 3,4-diiodophenyl, 3,5-diiodophenyl, 2,3-bis(trifluoromethyl)phenyl, 2,4-bis(trifluoromethyl)phenyl, 2,5-bis(trifluoromethyl)phenyl, 2,6-bis(trifluoromethyl)phenyl, 3,4-bis(trifluoromethyl)phenyl, 3,5-bis(trifluoromethyl)phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl and 2-chloro-5-trifluoromethylphenyl, preferably phenyl, 2-chlorophenyl, 2-methoxyphenyl, 3,5-dimethylphenyl, 3,5-bis(trifluoromethyl)phenyl, 3,5-dimethoxyphenyl, 2,5-dichlorophenyl and 2-chloro-5-trifluoromethylphenyl.

Specific examples of X include an oxygen atom, a sulfur atom, N—CN, N—NO$_2$, N—OMe, N—OEt and N—OBu, preferably an oxygen atom.

Specific examples of each of $R^1$ and $R^2$ include a hydrogen atom, fluorine, chlorine, bromine, iodine, methyl, ethyl, n-propyl, i-propyl, c-propyl, n-butyl, i-butyl, s-butyl, t-butyl, c-butyl, methoxy, ethoxy, n-propoxy, i-propoxy, c-propoxy, n-butoxy, i-butoxy, s-butoxy, t-butoxy and c-butoxy, preferably a hydrogen atom.

Specific examples of $R^3$ include phenyl, 4-fluorophenyl, 4-chlorophenyl, methoxy, ethoxy and benzyloxy, preferably 4-fluorophenyl and ethoxy.

Specific examples of each of $R^4$ and $R^5$ include a hydrogen atom, methyl, ethyl, n-propyl, i-propyl, c-propyl, n-butyl, i-butyl, s-butyl, t-butyl, c-butyl and benzyl, preferably a hydrogen atom, methyl and benzyl.

Specific examples of $R^6$ include a hydrogen atom, methyl, ethyl, n-propyl, i-propyl, c-propyl, n-butyl, i-butyl, s-butyl, t-butyl, c-butyl and benzyl, preferably a hydrogen atom, methyl and benzyl.

The following compounds may be mentioned as preferred compounds among the compounds of the formula (I) of the present invention.

(1) The compound of the formula (I) or its salt, wherein A is a single bond, $CH_2$, CHMe, $CH_2CH_2$ or $CH_2$CHMe, B is $CH_2CH_2$, $CH_2$CHMe, CHMeCH$_2$, CHMeCHMe, $CH_2CH_2CH_2$, CHMeCH$_2$CH$_2$, $CH_2$CHMeCH$_2$, $CH_2CH_2$CHMe, CHMeCHMeCH$_2$, CHMeCH$_2$CHMe, $CH_2$CHMeCHMe or CHMeCHMeCHMe, D is $CH_2$, CHMe, $CH_2CH_2$ or $CH_2$CHMe, E is $CH_2$, CHMe, $CH_2CH_2$ or $CH_2$CHMe, Ar is phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2-trifluoromethylphenyl, 3-trifluoromethylphenyl, 4-trifluoromethylphenyl, 2-methylphenyl, 3-methylphenyl, 4-methylphenyl, 2-methoxyphenyl, 3-methoxyphenyl, 4-methoxyphenyl, 2,3-difluorophenyl, 2,4-difluorophenyl, 2,5-difluorophenyl, 2,6-difluorophenyl, 3,4-difluorophenyl, 3,5-difluorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,3-dibromophenyl, 2,4-dibromophenyl, 2,5-dibromophenyl, 2,6-dibromophenyl, 3,4-dibromophenyl, 3,5-dibromophenyl, 2,3-diiodophenyl, 2,4-diiodophenyl, 2,5-diiodophenyl, 2,6-diiodophenyl, 3,4-diiodophenyl, 3,5-diiodophenyl, 2,3-bis(trifluoromethyl)phenyl, 2,4-bis(trifluoromethyl)phenyl, 2,5-bis(trifluoromethyl)phenyl, 2,6-bis(trifluoromethyl)phenyl, 3,4-bis(trifluoromethyl)phenyl, 3,5-bis(trifluoromethyl)phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl or 2-chloro-5-trifluoromethylphenyl, X is an oxygen atom, a sulfur atom, N—CN, N—NO$_2$, N—OMe, N—OEt or N—OBu, each of $R^1$ and $R^2$ is a hydrogen atom, fluorine, chlorine, bromine, iodine, methyl, ethyl, n-propyl, i-propyl, c-propyl, n-butyl, i-butyl, s-butyl, t-butyl, c-butyl, methoxy, ethoxy, n-propoxy, i-propoxy, c-propoxy, n-butoxy, i-butoxy, s-butoxy, t-butoxy or c-butoxy, $R^3$ is phenyl, 4-fluorophenyl, 4-chlorophenyl, methoxy, ethoxy or benzyloxy, each of $R^4$ and $R^5$ is a hydrogen atom, methyl, ethyl, n-propyl, i-propyl, c-propyl, n-butyl, i-butyl, s-butyl, t-butyl, c-butyl or benzyl, and $R^6$ is a hydrogen atom, methyl, ethyl, n-propyl, i-propyl, c-propyl, n-butyl, i-butyl, s-butyl, t-butyl, c-butyl or benzyl.

(2) The compound or its salt according to the above item (1), wherein X is an oxygen atom.

(3) The compound or its salt according to the above item (2), wherein each of $R^1$ and $R^2$ is a hydrogen atom.

(4) The compound of the formula (I) or its salt, wherein A is a single bond or $CH_2$, B is $CH_2CH_2$ or $CH_2CH_2CH_2$, D is $CH_2$, CHMe or $CH_2CH_2$, E is $CH_2$ or $CH_2CH_2$, Ar is phenyl, 2-chlorophenyl, 2-methoxyphenyl, 3,5-dimethylphenyl, 3,5-bis(trifluoromethyl)phenyl, 3,5-dimethoxyphenyl, 2,5-dichlorophenyl or 2-chloro-5-trifluoromethylphenyl, X is an oxygen atom, each of $R^1$ and $R^2$ is a hydrogen atom, $R^3$ is 4-fluorophenyl or ethoxy, each of $R^4$ and $R^5$ is a hydrogen atom, methyl or benzyl, and $R^6$ is a hydrogen atom, methyl or benzyl.

(5) The compound or its salt according to the above item (4), wherein E is $CH_2$, and $R^3$ is a 4-fluorophenyl group.

(6) The compound or its salt according to the above item (5), wherein Ar is 3,5-bistrifluoromethylphenyl.

Now, typical compounds among benzimidazole derivatives of the formula (Ia) as the compounds of the present invention will be presented in Table 1, but it should be understood that the present invention is by no means restricted to such specific compounds. In Table 1, Q1 to Q43 represent the groups of the following formulae:

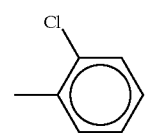
Q1

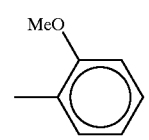
Q2

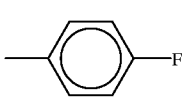
Q3

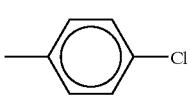
Q4

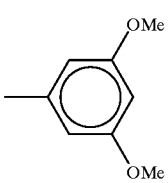
Q5

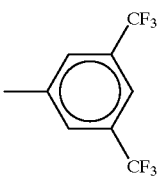
Q6

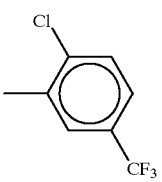
Q7

-continued

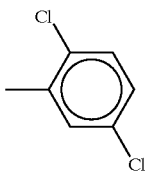
Q8

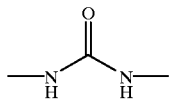
Q9

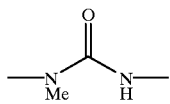
Q10

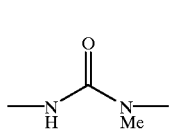
Q11

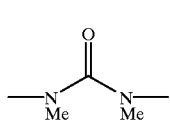
Q12

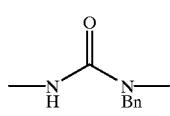
Q13

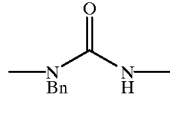
Q14

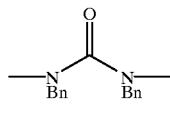
Q15

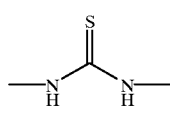
Q16

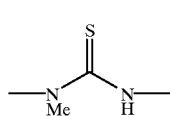
Q17

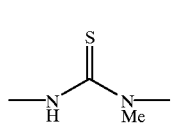
Q18

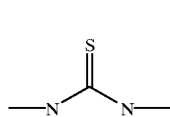
Q19

-continued

Q20 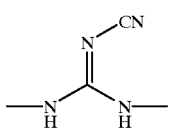

Q21 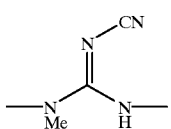

Q22 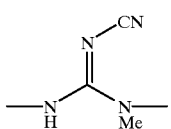

Q23 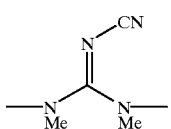

Q24 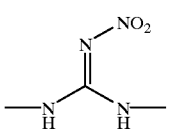

Q25 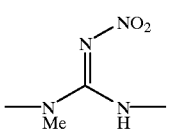

Q26 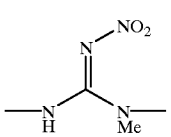

Q27 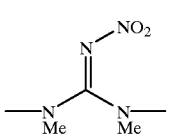

Q28 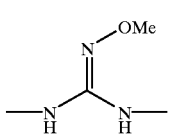

Q29 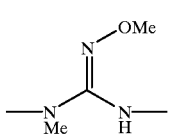

Q30 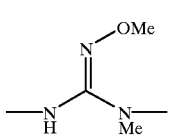

-continued

Q31 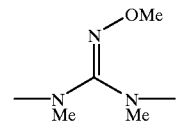

Q32 —CH$_2$·CH$_2$—

Q33 —CHMeCH$_2$—

Q34 —CH$_2$CHMe—

Q35 —CHMeCHMe—

Q36 —CH$_2$CH$_2$CH$_2$—

Q37 —CHMeCH$_2$CH$_2$—

Q38 —CH$_2$CHMeCH$_2$—

Q39 —CH$_2$CH$_2$CHMe—

Q40 —CHMeCHMeCH$_2$—

Q41 —CHMeCH$_2$CHMe—

Q42 —CH$_2$CHMeCHMe—

Q43 —CHMeCHMeCHMe—

Further, M in the Table has the following meaning:

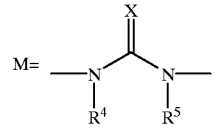

wherein $R^4$, $R^5$ and X are as defined above.

TABLE 1

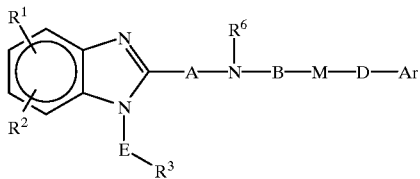

(Ia)

| A | B | D | E | M | Ar | $R^1$ | $R^2$ | $R^3$ | $R^6$ |
|---|---|---|---|---|---|---|---|---|---|
| — | Q32 | CH$_2$ | CH$_2$ | Q10 | Q1 | H | H | Q3 | Me |
| — | Q32 | CH$_2$ | CH$_2$ | Q10 | Q2 | H | H | Q3 | Me |
| — | Q32 | CH$_2$ | CH$_2$ | Q10 | Q3 | H | H | Q3 | Me |
| — | Q32 | CH$_2$ | CH$_2$ | Q10 | Q4 | H | H | Q3 | Me |
| — | Q32 | CH$_2$ | CH$_2$ | Q10 | Q5 | H | H | Q3 | Me |
| — | Q32 | CH$_2$ | CH$_2$ | Q10 | Q6 | H | H | Q3 | Me |
| — | Q32 | CH$_2$ | CH$_2$ | Q10 | Q7 | H | H | Q3 | Me |
| — | Q32 | CH$_2$ | CH$_2$ | Q10 | Q8 | H | H | Q3 | Me |
| CH$_2$ | Q32 | CH$_2$ | CH$_2$ | Q10 | Q1 | H | H | Q3 | Me |
| CH$_2$ | Q32 | CH$_2$ | CH$_2$ | Q10 | Q2 | H | H | Q3 | Me |
| CH$_2$ | Q32 | CH$_2$ | CH$_2$ | Q10 | Q3 | H | H | Q3 | Me |
| CH$_2$ | Q32 | CH$_2$ | CH$_2$ | Q10 | Q4 | H | H | Q3 | Me |

TABLE 1-continued

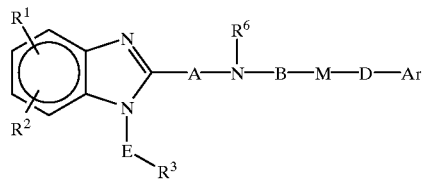

(Ia)

| A | B | D | E | M | Ar | R¹ | R² | R³ | R⁶ |
|---|---|---|---|---|---|---|---|---|---|
| CH₂ | Q32 | CH₂ | CH₂ | Q10 | Q5 | H | H | Q3 | Me |
| CH₂ | Q32 | CH₂ | CH₂ | Q10 | Q6 | H | H | Q3 | Me |
| CH₂ | Q32 | CH₂ | CH₂ | Q10 | Q7 | H | H | Q3 | Me |
| CH₂ | Q32 | CH₂ | CH₂ | Q10 | Q8 | H | H | Q3 | Me |
| — | Q38 | CH₂ | CH₂ | Q10 | Q1 | H | H | Q3 | Me |
| — | Q36 | CH₂ | CH₂ | Q10 | Q2 | H | H | Q3 | Me |
| — | Q36 | CH₂ | CH₂ | Q10 | Q3 | H | H | Q3 | Me |
| — | Q36 | CH₂ | CH₂ | Q10 | Q4 | H | H | Q3 | Me |
| — | Q36 | CH₂ | CH₂ | Q10 | Q5 | H | H | Q3 | Me |
| — | Q36 | CH₂ | CH₂ | Q10 | Q6 | H | H | Q3 | Me |
| — | Q36 | CH₂ | CH₂ | Q10 | Q7 | H | H | Q3 | Me |
| — | Q36 | CH₂ | CH₂ | Q10 | Q8 | H | H | Q3 | Me |
| CH₂ | Q36 | CH₂ | CH₂ | Q10 | Q1 | H | H | Q3 | Me |
| CH₂ | Q36 | CH₂ | CH₂ | Q10 | Q2 | H | H | Q3 | Me |
| CH₂ | Q36 | CH₂ | CH₂ | Q10 | Q3 | H | H | Q3 | Me |
| CH₂ | Q36 | CH₂ | CH₂ | Q10 | Q4 | H | H | Q3 | Me |
| CH₂ | Q36 | CH₂ | CH₂ | Q10 | Q5 | H | H | Q3 | Me |
| CH₂ | Q36 | CH₂ | CH₂ | Q10 | Q6 | H | H | Q3 | Me |
| CH₂ | Q36 | CH₂ | CH₂ | Q10 | Q7 | H | H | Q3 | Me |
| CH₂ | Q36 | CH₂ | CH₂ | Q10 | Q8 | H | H | Q3 | Me |
| — | Q32 | CH₂ | CH₂ | Q10 | Q1 | H | H | Ph | Me |
| — | Q32 | CH₂ | CH₂ | Q10 | Q2 | H | H | Ph | Me |
| — | Q32 | CH₂ | CH₂ | Q10 | Q3 | H | H | Ph | Me |
| — | Q32 | CH₂ | CH₂ | Q10 | Q4 | H | H | Ph | Me |
| — | Q32 | CH₂ | CH₂ | Q10 | Q5 | H | H | Ph | Me |
| — | Q32 | CH₂ | CH₂ | Q10 | Q6 | H | H | Ph | Me |
| — | Q32 | CH₂ | CH₂ | Q10 | Q7 | H | H | Ph | Me |
| — | Q32 | CH₂ | CH₂ | Q10 | Q8 | H | H | Ph | Me |
| CH₂ | Q32 | CH₂ | CH₂ | Q10 | Q1 | H | H | Ph | Me |
| CH₂ | Q32 | CH₂ | CH₂ | Q10 | Q2 | H | H | Ph | Me |
| CH₂ | Q32 | CH₂ | CH₂ | Q10 | Q3 | H | H | Ph | Me |
| CH₂ | Q32 | CH₂ | CH₂ | Q10 | Q4 | H | H | Ph | Me |
| CH₂ | Q32 | CH₂ | CH₂ | Q10 | Q5 | H | H | Ph | Me |
| CH₂ | Q32 | CH₂ | CH₂ | Q10 | Q6 | H | H | Ph | Me |
| CH₂ | Q32 | CH₂ | CH₂ | Q10 | Q7 | H | H | Ph | Me |
| CH₂ | Q32 | CH₂ | CH₂ | Q10 | Q8 | H | H | Ph | Me |
| — | Q36 | CH₂ | CH₂ | Q10 | Q1 | H | H | Ph | Me |
| — | Q36 | CH₂ | CH₂ | Q10 | Q2 | H | H | Ph | Me |
| — | Q36 | CH₂ | CH₂ | Q10 | Q3 | H | H | Ph | Me |
| — | Q36 | CH₂ | CH₂ | Q10 | Q4 | H | H | Ph | Me |
| — | Q36 | CH₂ | CH₂ | Q10 | Q5 | H | H | Ph | Me |
| — | Q36 | CH₂ | CH₂ | Q10 | Q6 | H | H | Ph | Me |
| — | Q36 | CH₂ | CH₂ | Q10 | Q7 | H | H | Ph | Me |
| — | Q36 | CH₂ | CH₂ | Q10 | Q8 | H | H | Ph | Me |
| CH₂ | Q36 | CH₂ | CH₂ | Q10 | Q1 | H | H | Ph | Me |
| CH₂ | Q36 | CH₂ | CH₂ | Q10 | Q2 | H | H | Ph | Me |
| CH₂ | Q36 | CH₂ | CH₂ | Q10 | Q3 | H | H | Ph | Me |
| CH₂ | Q36 | CH₂ | CH₂ | Q10 | Q4 | H | H | Ph | Me |
| CH₂ | Q36 | CH₂ | CH₂ | Q10 | Q5 | H | H | Ph | Me |
| CH₂ | Q36 | CH₂ | CH₂ | Q10 | Q6 | H | H | Ph | Me |
| CH₂ | Q36 | CH₂ | CH₂ | Q10 | Q7 | H | H | Ph | Me |
| CH₂ | Q36 | CH₂ | CH₂ | Q10 | Q8 | H | H | Ph | Me |
| — | Q32 | CH₂ | CH₂ | Q10 | Q1 | H | H | Q4 | Me |
| — | Q32 | CH₂ | CH₂ | Q10 | Q2 | H | H | Q4 | Me |
| — | Q32 | CH₂ | CH₂ | Q10 | Q3 | H | H | Q4 | Me |
| — | Q32 | CH₂ | CH₂ | Q10 | Q4 | H | H | Q4 | Me |
| — | Q32 | CH₂ | CH₂ | Q10 | Q5 | H | H | Q4 | Me |
| — | Q32 | CH₂ | CH₂ | Q10 | Q6 | H | H | Q4 | Me |
| — | Q32 | CH₂ | CH₂ | Q10 | Q7 | H | H | Q4 | Me |
| — | Q32 | CH₂ | CH₂ | Q10 | Q8 | H | H | Q4 | Me |
| CH₂ | Q32 | CH₂ | CH₂ | Q10 | Q1 | H | h | Q4 | Me |
| CH₂ | Q32 | CH₂ | CH₂ | Q10 | Q2 | H | H | Q4 | Me |
| CH₂ | Q32 | CH₂ | CH₂ | Q10 | Q3 | H | H | Q4 | Me |
| CH₂ | Q32 | CH₂ | CH₂ | Q10 | Q4 | H | H | Q4 | Me |
| CH₂ | Q32 | CH₂ | CH₂ | Q10 | Q5 | H | H | Q4 | Me |
| CH₂ | Q32 | CH₂ | CH₂ | Q10 | Q6 | H | H | Q4 | Me |
| CH₂ | Q32 | CH₂ | CH₂ | Q10 | Q7 | H | H | Q4 | Me |
| CH₂ | Q32 | CH₂ | CH₂ | Q10 | Q8 | H | H | Q4 | Me |
| — | Q36 | CH₂ | CH₂ | Q10 | Q1 | H | H | Q4 | Me |
| — | Q36 | CH₂ | CH₂ | Q10 | Q2 | H | H | Q4 | Me |
| — | Q36 | CH₂ | CH₂ | Q10 | Q3 | H | H | Q4 | Me |
| — | Q36 | CH₂ | CH₂ | Q10 | Q4 | H | H | Q4 | Me |
| — | Q36 | CH₂ | CH₂ | Q10 | Q5 | H | H | Q4 | Me |
| — | Q36 | CH₂ | CH₂ | Q10 | Q6 | H | H | Q4 | Me |
| — | Q36 | CH₂ | CH₂ | Q10 | Q7 | H | H | Q4 | Me |
| — | Q36 | CH₂ | CH₂ | Q10 | Q8 | H | H | Q4 | Me |
| CH₂ | Q36 | CH₂ | CH₂ | Q10 | Q1 | H | H | Q4 | Me |
| CH₂ | Q36 | CH₂ | CH₂ | Q10 | Q2 | H | H | Q4 | Me |
| CH₂ | Q36 | CH₂ | CH₂ | Q10 | Q3 | H | H | Q4 | Me |
| CH₂ | Q36 | CH₂ | CH₂ | Q10 | Q4 | H | H | Q4 | Me |
| CH₂ | Q36 | CH₂ | CH₂ | Q10 | Q5 | H | H | Q4 | Me |
| CH₂ | Q36 | CH₂ | CH₂ | Q10 | Q6 | H | H | Q4 | Me |
| CH₂ | Q36 | CH₂ | CH₂ | Q10 | Q7 | H | H | Q4 | Me |
| CH₂ | Q36 | CH₂ | CH₂ | Q10 | Q8 | H | H | Q4 | Me |
| — | Q32 | CH₂ | CH₂ | Q10 | Q1 | H | H | Q3 | H |
| — | Q32 | CH₂ | CH₂ | Q10 | Q2 | H | H | Q3 | H |
| — | Q32 | CH₂ | CH₂ | Q10 | Q3 | H | H | Q3 | H |
| — | Q32 | CH₂ | CH₂ | Q10 | Q4 | H | H | Q3 | H |
| — | Q32 | CH₂ | CH₂ | Q10 | Q5 | H | H | Q3 | H |
| — | Q32 | CH₂ | CH₂ | Q10 | Q6 | H | H | Q3 | H |
| — | Q32 | CH₂ | CH₂ | Q10 | Q7 | H | H | Q3 | H |
| — | Q32 | CH₂ | CH₂ | Q10 | Q8 | H | H | Q3 | H |
| CH₂ | Q32 | CH₂ | CH₂ | Q10 | Q1 | H | H | Q3 | H |
| CH₂ | Q32 | CH₂ | CH₂ | Q10 | Q2 | H | H | Q3 | H |
| CH₂ | Q32 | CH₂ | CH₂ | Q10 | Q3 | H | H | Q3 | H |
| CH₂ | Q32 | CH₂ | CH₂ | Q10 | Q4 | H | H | Q3 | H |
| CH₂ | Q32 | CH₂ | CH₂ | Q10 | Q5 | H | H | Q3 | H |
| CH₂ | Q32 | CH₂ | CH₂ | Q10 | Q6 | H | H | Q3 | H |
| CH₂ | Q32 | CH₂ | CH₂ | Q10 | Q7 | H | H | Q3 | H |
| CH₂ | Q32 | CH₂ | CH₂ | Q10 | Q8 | H | H | Q3 | H |
| — | Q36 | CH₂ | CH₂ | Q10 | Q1 | H | H | Q3 | H |
| — | Q36 | CH₂ | CH₂ | Q10 | Q2 | H | H | Q3 | H |
| — | Q36 | CH₂ | CH₂ | Q10 | Q3 | H | H | Q3 | H |
| — | Q36 | CH₂ | CH₂ | Q10 | Q4 | H | H | Q3 | H |
| — | Q36 | CH₂ | CH₂ | Q10 | Q5 | H | H | Q3 | H |
| — | Q36 | CH₂ | CH₂ | Q10 | Q6 | H | H | Q3 | H |
| — | Q36 | CH₂ | CH₂ | Q10 | Q7 | H | H | Q3 | H |
| — | Q36 | CH₂ | CH₂ | Q10 | Q8 | H | H | Q3 | H |
| CH₂ | Q36 | CH₂ | CH₂ | Q10 | Q1 | H | H | Q3 | H |
| CH₂ | Q36 | CH₂ | CH₂ | Q10 | Q2 | H | H | Q3 | H |
| CH₂ | Q36 | CH₂ | CH₂ | Q10 | Q3 | H | H | Q3 | H |
| CH₂ | Q36 | CH₂ | CH₂ | Q10 | Q4 | H | H | Q3 | H |
| CH₂ | Q36 | CH₂ | CH₂ | Q10 | Q5 | H | H | Q3 | H |
| CH₂ | Q36 | CH₂ | CH₂ | Q10 | Q6 | H | H | Q3 | H |
| CH₂ | Q36 | CH₂ | CH₂ | Q10 | Q7 | H | H | Q3 | H |
| CH₂ | Q36 | CH₂ | CH₂ | Q10 | Q8 | H | H | Q3 | H |
| — | Q32 | CH₂ | Q9 | Q1 | H | H | Q3 | Me |
| — | Q32 | CH₂ | Q9 | Q2 | H | H | Q3 | Me |
| — | Q32 | CH₂ | Q9 | Q3 | H | H | Q3 | Me |
| — | Q32 | CH₂ | Q9 | Q4 | H | H | Q3 | Me |
| — | Q32 | CH₂ | Q9 | Q5 | H | H | Q3 | Me |
| — | Q32 | CH₂ | Q9 | Q6 | H | H | Q3 | Me |
| — | Q32 | CH₂ | Q9 | Q7 | H | H | Q3 | Me |
| — | Q32 | CH₂ | Q9 | Q8 | H | H | Q3 | Me |
| CH₂ | Q32 | CH₂ | Q9 | Q1 | H | H | Q3 | Me |
| CH₂ | Q32 | CH₂ | Q9 | Q2 | H | H | Q3 | Me |
| CH₂ | Q32 | CH₂ | Q9 | Q3 | H | H | Q3 | Me |
| CH₂ | Q32 | CH₂ | Q9 | Q4 | H | H | Q3 | Me |
| CH₂ | Q32 | CH₂ | Q9 | Q5 | H | H | Q3 | Me |
| CH₂ | Q32 | CH₂ | Q9 | Q6 | H | H | Q3 | Me |
| CH₂ | Q32 | CH₂ | Q9 | Q7 | H | H | Q3 | Me |
| CH₂ | Q32 | CH₂ | Q9 | Q8 | H | H | Q3 | Me |

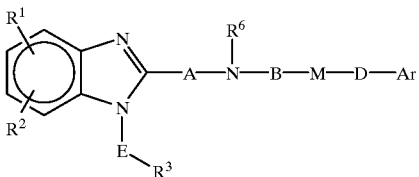

TABLE 1-continued (Ia)

| A | B | D | E | M | Ar | R$^1$ | R$^2$ | R$^3$ | R$^6$ |
|---|---|---|---|---|---|---|---|---|---|
| — | Q36 | CH$_2$ | CH$_2$ | Q9 | Q1 | H | H | Q3 | Me |
| — | Q36 | CH$_2$ | CH$_2$ | Q9 | Q2 | H | H | Q3 | Me |
| — | Q36 | CH$_2$ | CH$_2$ | Q9 | Q3 | H | H | Q3 | Me |
| — | Q36 | CH$_2$ | CH$_2$ | Q9 | Q4 | H | H | Q3 | Me |
| — | Q36 | CH$_2$ | CH$_2$ | Q9 | Q5 | H | H | Q3 | Me |
| — | Q36 | CH$_2$ | CH$_2$ | Q9 | Q6 | H | H | Q3 | Me |
| — | Q36 | CH$_2$ | CH$_2$ | Q9 | Q7 | H | H | Q3 | Me |
| — | Q36 | CH$_2$ | CH$_2$ | Q9 | Q8 | H | H | Q3 | Me |
| CH$_2$ | Q36 | CH$_2$ | CH$_2$ | Q9 | Q1 | H | H | Q3 | Me |
| CH$_2$ | Q36 | CH$_2$ | CH$_2$ | Q9 | Q2 | H | H | Q3 | Me |
| CH$_2$ | Q36 | CH$_2$ | CH$_2$ | Q9 | Q3 | H | H | Q3 | Me |
| CH$_2$ | Q36 | CH$_2$ | CH$_2$ | Q9 | Q4 | H | H | Q3 | Me |
| CH$_2$ | Q36 | CH$_2$ | CH$_2$ | Q9 | Q5 | H | H | Q3 | Me |
| CH$_2$ | Q36 | CH$_2$ | CH$_2$ | Q9 | Q6 | H | H | Q3 | Me |
| CH$_2$ | Q36 | CH$_2$ | CH$_2$ | Q9 | Q7 | H | H | Q3 | Me |
| CH$_2$ | Q36 | CH$_2$ | CH$_2$ | Q9 | Q8 | H | H | Q3 | Me |
| — | Q32 | CH$_2$ | CH$_2$ | Q11 | Q1 | H | H | Q3 | Me |
| — | Q32 | CH$_2$ | CH$_2$ | Q11 | Q2 | H | H | Q3 | Me |
| — | Q32 | CH$_2$ | CH$_2$ | Q11 | Q3 | H | H | Q3 | Me |
| — | Q32 | CH$_2$ | CH$_2$ | Q11 | Q4 | H | H | Q3 | Me |
| — | Q32 | CH$_2$ | CH$_2$ | Q11 | Q5 | H | H | Q3 | Me |
| — | Q32 | CH$_2$ | CH$_2$ | Q11 | Q6 | H | H | Q3 | Me |
| — | Q32 | CH$_2$ | CH$_2$ | Q11 | Q7 | H | H | Q3 | Me |
| — | Q32 | CH$_2$ | CH$_2$ | Q11 | Q8 | H | H | Q3 | Me |
| CH$_2$ | Q32 | CH$_2$ | CH$_2$ | Q11 | Q1 | H | H | Q3 | Me |
| CH$_2$ | Q32 | CH$_2$ | CH$_2$ | Q11 | Q2 | H | H | Q3 | Me |
| CH$_2$ | Q32 | CH$_2$ | CH$_2$ | Q11 | Q3 | H | H | Q3 | Me |
| CH$_2$ | Q32 | CH$_2$ | CH$_2$ | Q11 | Q4 | H | H | Q3 | Me |
| CH$_2$ | Q32 | CH$_2$ | CH$_2$ | Q11 | Q5 | H | H | Q3 | Me |
| CH$_2$ | Q32 | CH$_2$ | CH$_2$ | Q11 | Q6 | H | H | Q3 | Me |
| CH$_2$ | Q32 | CH$_2$ | CH$_2$ | Q11 | Q7 | H | H | Q3 | Me |
| CH$_2$ | Q32 | CH$_2$ | CH$_2$ | Q11 | Q8 | H | H | Q3 | Me |
| — | Q36 | CH$_2$ | CH$_2$ | Q11 | Q1 | H | H | Q3 | Me |
| — | Q36 | CH$_2$ | CH$_2$ | Q11 | Q2 | H | H | Q3 | Me |
| — | Q36 | CH$_2$ | CH$_2$ | Q11 | Q3 | H | H | Q3 | Me |
| — | Q36 | CH$_2$ | CH$_2$ | Q11 | Q4 | H | H | Q3 | Me |
| — | Q36 | CH$_2$ | CH$_2$ | Q11 | Q5 | H | H | Q3 | Me |
| — | Q36 | CH$_2$ | CH$_2$ | Q11 | Q6 | H | H | Q3 | Me |
| — | Q36 | CH$_2$ | CH$_2$ | Q11 | Q7 | H | H | Q3 | Me |
| — | Q36 | CH$_2$ | CH$_2$ | Q11 | Q8 | H | H | Q3 | Me |
| CH$_2$ | Q36 | CH$_2$ | CH$_2$ | Q11 | Q1 | H | H | Q3 | Me |
| CH$_2$ | Q36 | CH$_2$ | CH$_2$ | Q11 | Q2 | H | H | Q3 | Me |
| CH$_2$ | Q36 | CH$_2$ | CH$_2$ | Q11 | Q3 | H | H | Q3 | Me |
| CH$_2$ | Q36 | CH$_2$ | CH$_2$ | Q11 | Q4 | H | H | Q3 | Me |
| CH$_2$ | Q36 | CH$_2$ | CH$_2$ | Q11 | Q5 | H | H | Q3 | Me |
| CH$_2$ | Q36 | CH$_2$ | CH$_2$ | Q11 | Q6 | H | H | Q3 | Me |
| CH$_2$ | Q36 | CH$_2$ | CH$_2$ | Q11 | Q7 | H | H | Q3 | Me |
| CH$_2$ | Q36 | CH$_2$ | CH$_2$ | Q11 | Q8 | H | H | Q3 | Me |
| — | Q32 | CH$_2$ | CH$_2$ | Q12 | Q1 | H | H | Q3 | Me |
| — | Q32 | CH$_2$ | CH$_2$ | Q12 | Q2 | H | H | Q3 | Me |
| — | Q32 | CH$_2$ | CH$_2$ | Q12 | Q3 | H | H | Q3 | Me |
| — | Q32 | CH$_2$ | CH$_2$ | Q12 | Q4 | H | H | Q3 | Me |
| — | Q32 | CH$_2$ | CH$_2$ | Q12 | Q5 | H | H | Q3 | Me |
| — | Q32 | CH$_2$ | CH$_2$ | Q12 | Q6 | H | H | Q3 | Me |
| — | Q32 | CH$_2$ | CH$_2$ | Q12 | Q7 | H | H | Q3 | Me |
| — | Q32 | CH$_2$ | CH$_2$ | Q12 | Q8 | H | H | Q3 | Me |
| CH$_2$ | Q32 | CH$_2$ | CH$_2$ | Q12 | Q1 | H | H | Q3 | Me |
| CH$_2$ | Q32 | CH$_2$ | CH$_2$ | Q12 | Q2 | H | H | Q3 | Me |
| CH$_2$ | Q32 | CH$_2$ | CH$_2$ | Q12 | Q3 | H | H | Q3 | Me |
| CH$_2$ | Q32 | CH$_2$ | CH$_2$ | Q12 | Q4 | H | H | Q3 | Me |
| CH$_2$ | Q32 | CH$_2$ | CH$_2$ | Q12 | Q5 | H | H | Q3 | Me |
| CH$_2$ | Q32 | CH$_2$ | CH$_2$ | Q12 | Q6 | H | H | Q3 | Me |
| CH$_2$ | Q32 | CH$_2$ | CH$_2$ | Q12 | Q7 | H | H | Q3 | Me |
| CH$_2$ | Q32 | CH$_2$ | CH$_2$ | Q12 | Q8 | H | H | Q3 | Me |
| — | Q36 | CH$_2$ | CH$_2$ | Q12 | Q1 | H | H | Q3 | Me |
| — | Q36 | CH$_2$ | CH$_2$ | Q12 | Q2 | H | H | Q3 | Me |
| — | Q36 | CH$_2$ | CH$_2$ | Q12 | Q3 | H | H | Q3 | Me |
| — | Q36 | CH$_2$ | CH$_2$ | Q12 | Q4 | H | H | Q3 | Me |
| — | Q36 | CH$_2$ | CH$_2$ | Q12 | Q5 | H | H | Q3 | Me |
| — | Q36 | CH$_2$ | CH$_2$ | Q12 | Q6 | H | H | Q3 | Me |
| — | Q36 | CH$_2$ | CH$_2$ | Q12 | Q7 | H | H | Q3 | Me |
| — | Q36 | CH$_2$ | CH$_2$ | Q12 | Q8 | H | H | Q3 | Me |
| CH$_2$ | Q36 | CH$_2$ | CH$_2$ | Q12 | Q1 | H | H | Q3 | Me |
| CH$_2$ | Q36 | CH$_2$ | CH$_2$ | Q12 | Q2 | H | H | Q3 | Me |
| CH$_2$ | Q36 | CH$_2$ | CH$_2$ | Q12 | Q3 | H | H | Q3 | Me |
| CH$_2$ | Q36 | CH$_2$ | CH$_2$ | Q12 | Q4 | H | H | Q3 | Me |
| CH$_2$ | Q36 | CH$_2$ | CH$_2$ | Q12 | Q5 | H | H | Q3 | Me |
| CH$_2$ | Q36 | CH$_2$ | CH$_2$ | Q12 | Q6 | H | H | Q3 | Me |
| CH$_2$ | Q36 | CH$_2$ | CH$_2$ | Q12 | Q7 | H | H | Q3 | Me |
| CH$_2$ | Q36 | CH$_2$ | CH$_2$ | Q12 | Q8 | H | H | Q3 | Me |
| — | Q32 | CHMe | CH$_2$ | Q10 | Q1 | H | H | Q3 | Me |
| — | Q32 | CHMe | CH$_2$ | Q10 | Q2 | H | H | Q3 | Me |
| — | Q32 | CHMe | CH$_2$ | Q10 | Q3 | H | H | Q3 | Me |
| — | Q32 | CHMe | CH$_2$ | Q10 | Q4 | H | H | Q3 | Me |
| — | Q32 | CHMe | CH$_2$ | Q10 | Q5 | H | H | Q3 | Me |
| — | Q32 | CHMe | CH$_2$ | Q10 | Q6 | H | H | Q3 | Me |
| — | Q32 | CHMe | CH$_2$ | Q10 | Q7 | H | H | Q3 | Me |
| — | Q32 | CHMe | CH$_2$ | Q10 | Q8 | H | H | Q3 | Me |
| CH$_2$ | Q32 | CHMe | CH$_2$ | Q10 | Q1 | H | H | Q3 | Me |
| CH$_2$ | Q32 | CHMe | CH$_2$ | Q10 | Q2 | H | H | Q3 | Me |
| CH$_2$ | Q32 | CHMe | CH$_2$ | Q10 | Q3 | H | H | Q3 | Me |
| CH$_2$ | Q32 | CHMe | CH$_2$ | Q10 | Q4 | H | H | Q3 | Me |
| CH$_2$ | Q32 | CHMe | CH$_2$ | Q10 | Q5 | H | H | Q3 | Me |
| CH$_2$ | Q32 | CHMe | CH$_2$ | Q10 | Q6 | H | H | Q3 | Me |
| CH$_2$ | Q32 | CHMe | CH$_2$ | Q10 | Q7 | H | H | Q3 | Me |
| CH$_2$ | Q32 | CHMe | CH$_2$ | Q10 | Q8 | H | H | Q3 | Me |
| — | Q36 | CHMe | CH$_2$ | Q10 | Q1 | H | H | Q3 | Me |
| — | Q36 | CHMe | CH$_2$ | Q10 | Q2 | H | H | Q3 | Me |
| — | Q36 | CHMe | CH$_2$ | Q10 | Q3 | H | H | Q3 | Me |
| — | Q36 | CHMe | CH$_2$ | Q10 | Q4 | H | H | Q3 | Me |
| — | Q36 | CHMe | CH$_2$ | Q10 | Q5 | H | H | Q3 | Me |
| — | Q36 | CHMe | CH$_2$ | Q10 | Q6 | H | H | Q3 | Me |
| — | Q36 | CHMe | CH$_2$ | Q10 | Q7 | H | H | Q3 | Me |
| — | Q36 | CHMe | CH$_2$ | Q10 | Q8 | H | H | Q3 | Me |
| CH$_2$ | Q36 | CHMe | CH$_2$ | Q10 | Q1 | H | H | Q3 | Me |
| CH$_2$ | Q36 | CHMe | CH$_2$ | Q10 | Q2 | H | H | Q3 | Me |
| CH$_2$ | Q36 | CHMe | CH$_2$ | Q10 | Q3 | H | H | Q3 | Me |
| CH$_2$ | Q36 | CHMe | CH$_2$ | Q10 | Q4 | H | H | Q3 | Me |
| CH$_2$ | Q36 | CHMe | CH$_2$ | Q10 | Q5 | H | H | Q3 | Me |
| CH$_2$ | Q36 | CHMe | CH$_2$ | Q10 | Q6 | H | H | Q3 | Me |
| CH$_2$ | Q36 | CHMe | CH$_2$ | Q10 | Q7 | H | H | Q3 | Me |
| CH$_2$ | Q36 | CHMe | CH$_2$ | Q10 | Q8 | H | H | Q3 | Me |
| — | Q32 | CH$_2$ | CH$_2$ | Q13 | Q1 | H | H | Q3 | Me |
| — | Q32 | CH$_2$ | CH$_2$ | Q13 | Q2 | H | H | Q3 | Me |
| — | Q32 | CH$_2$ | CH$_2$ | Q13 | Q6 | H | H | Q3 | Me |
| CH$_2$ | Q32 | CH$_2$ | CH$_2$ | Q13 | Q1 | H | H | Q3 | Me |
| CH$_2$ | Q32 | CH$_2$ | CH$_2$ | Q13 | Q2 | H | H | Q3 | Me |
| CH$_2$ | Q32 | CH$_2$ | CH$_2$ | Q13 | Q6 | H | H | Q3 | Me |
| — | Q36 | CH$_2$ | CH$_2$ | Q13 | Q1 | H | H | Q3 | Me |
| — | Q36 | CH$_2$ | CH$_2$ | Q13 | Q2 | H | H | Q3 | Me |
| — | Q36 | CH$_2$ | CH$_2$ | Q13 | Q6 | H | H | Q3 | Me |
| CH$_2$ | Q36 | CH$_2$ | CH$_2$ | Q13 | Q1 | H | H | Q3 | Me |
| CH$_2$ | Q36 | CH$_2$ | CH$_2$ | Q13 | Q2 | H | H | Q3 | Me |
| CH$_2$ | Q36 | CH$_2$ | CH$_2$ | Q13 | Q6 | H | H | Q3 | Me |
| — | Q32 | CH$_2$ | CH$_2$ | Q14 | Q1 | H | H | Q3 | Me |
| — | Q32 | CH$_2$ | CH$_2$ | Q14 | Q2 | H | H | Q3 | Me |
| — | Q32 | CH$_2$ | CH$_2$ | Q14 | Q6 | H | H | Q3 | Me |
| CH$_2$ | Q32 | CH$_2$ | CH$_2$ | Q14 | Q1 | H | H | Q3 | Me |
| CH$_2$ | Q32 | CH$_2$ | CH$_2$ | Q14 | Q2 | H | H | Q3 | Me |
| CH$_2$ | Q32 | CH$_2$ | CH$_2$ | Q14 | Q6 | H | H | Q3 | Me |
| — | Q36 | CH$_2$ | CH$_2$ | Q14 | Q1 | H | H | Q3 | Me |
| — | Q36 | CH$_2$ | CH$_2$ | Q14 | Q2 | H | H | Q3 | Me |

TABLE 1-continued

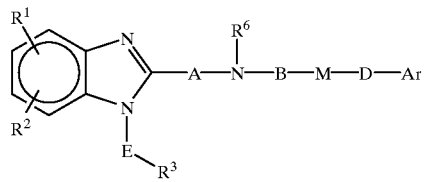

(Ia)

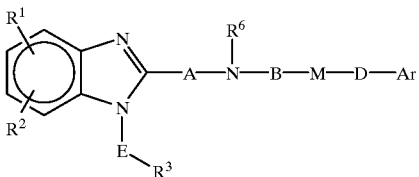

(Ia)

| A | B | D | E | M | Ar | R$^1$ | R$^2$ | R$^3$ | R$^6$ | A | B | D | E | M | Ar | R$^1$ | R$^2$ | R$^3$ | R$^6$ |
|---|---|---|---|---|---|---|---|---|---|---|---|---|---|---|---|---|---|---|---|
| — | Q36 | CH$_2$ | CH$_2$ | Q14 | Q6 | H | H | Q3 | Me | — | Q36 | CH$_2$ | CH$_2$ | Q28 | Q6 | H | H | Q3 | Me |
| CH$_2$ | Q36 | CH$_2$ | CH$_2$ | Q14 | Q1 | H | H | Q3 | Me | CH$_2$ | Q36 | CH$_2$ | CH$_2$ | Q28 | Q6 | H | H | Q3 | Me |
| CH$_2$ | Q36 | CH$_2$ | CH$_2$ | Q14 | Q2 | H | H | Q3 | Me | — | Q32 | CH$_2$ | CH$_2$ | Q29 | Q6 | H | H | Q3 | Me |
| CH$_2$ | Q36 | CH$_2$ | CH$_2$ | Q14 | Q6 | H | H | Q3 | Me | CH$_2$ | Q32 | CH$_2$ | CH$_2$ | Q29 | Q6 | H | H | Q3 | Me |
| — | Q32 | CH$_2$ | CH$_2$ | Q15 | Q1 | H | H | Q3 | Me | — | Q36 | CH$_2$ | CH$_2$ | Q29 | Q6 | H | H | Q3 | Me |
| — | Q32 | CH$_2$ | CH$_2$ | Q15 | Q2 | H | H | Q3 | Me | CH$_2$ | Q36 | CH$_2$ | CH$_2$ | Q29 | Q6 | H | H | Q3 | Me |
| — | Q32 | CH$_2$ | CH$_2$ | Q15 | Q6 | H | H | Q3 | Me | — | Q32 | CH$_2$ | CH$_2$ | Q30 | Q6 | H | H | Q3 | Me |
| CH$_2$ | Q32 | CH$_2$ | CH$_2$ | Q15 | Q1 | H | H | Q3 | Me | CH$_2$ | Q32 | CH$_2$ | CH$_2$ | Q30 | Q6 | H | H | Q3 | Me |
| CH$_2$ | Q32 | CH$_2$ | CH$_2$ | Q15 | Q2 | H | H | Q3 | Me | — | Q36 | CH$_2$ | CH$_2$ | Q30 | Q6 | H | H | Q3 | Me |
| CH$_2$ | Q32 | CH$_2$ | CH$_2$ | Q15 | Q6 | H | H | Q3 | Me | CH$_2$ | Q36 | CH$_2$ | CH$_2$ | Q30 | Q6 | H | H | Q3 | Me |
| — | Q36 | CH$_2$ | CH$_2$ | Q15 | Q1 | H | H | Q3 | Me | — | Q32 | CH$_2$ | CH$_2$ | Q31 | Q6 | H | H | Q3 | Me |
| — | Q36 | CH$_2$ | CH$_2$ | Q15 | Q2 | H | H | Q3 | Me | CH$_2$ | Q32 | CH$_2$ | CH$_2$ | Q31 | Q6 | H | H | Q3 | Me |
| — | Q36 | CH$_2$ | CH$_2$ | Q15 | Q6 | H | H | Q3 | Me | — | Q36 | CH$_2$ | CH$_2$ | Q31 | Q6 | H | H | Q3 | Me |
| CH$_2$ | Q36 | CH$_2$ | CH$_2$ | Q15 | Q1 | H | H | Q3 | Me | CH$_2$ | Q36 | CH$_2$ | CH$_2$ | Q31 | Q6 | H | H | Q3 | Me |
| CH$_2$ | Q36 | CH$_2$ | CH$_2$ | Q15 | Q2 | H | H | Q3 | Me | — | Q33 | CH$_2$ | CH$_2$ | Q10 | Q6 | H | H | Q3 | Me |
| CH$_2$ | Q36 | CH$_2$ | CH$_2$ | Q15 | Q6 | H | H | Q3 | Me | CH$_2$ | Q33 | CH$_2$ | CH$_2$ | Q10 | Q6 | H | H | Q3 | Me |
| — | Q32 | CH$_2$ | CH$_2$ | Q16 | Q6 | H | H | Q3 | Me | — | Q34 | CH$_2$ | CH$_2$ | Q10 | Q6 | H | H | Q3 | Me |
| CH$_2$ | Q32 | CH$_2$ | CH$_2$ | Q16 | Q6 | H | H | Q3 | Me | CH$_2$ | Q34 | CH$_2$ | CH$_2$ | Q10 | Q6 | H | H | Q3 | Me |
| — | Q36 | CH$_2$ | CH$_2$ | Q16 | Q6 | H | H | Q3 | Me | — | Q35 | CH$_2$ | CH$_2$ | Q10 | Q6 | H | H | Q3 | Me |
| CH$_2$ | Q36 | CH$_2$ | CH$_2$ | Q16 | Q6 | H | H | Q3 | Me | CH$_2$ | Q35 | CH$_2$ | CH$_2$ | Q10 | Q6 | H | H | Q3 | Me |
| — | Q32 | CH$_2$ | CH$_2$ | Q17 | Q6 | H | H | Q3 | Me | — | Q37 | CH$_2$ | CH$_2$ | Q10 | Q6 | H | H | Q3 | Me |
| CH$_2$ | Q32 | CH$_2$ | CH$_2$ | Q17 | Q6 | H | H | Q3 | Me | CH$_2$ | Q37 | CH$_2$ | CH$_2$ | Q10 | Q6 | H | H | Q3 | Me |
| — | Q36 | CH$_2$ | CH$_2$ | Q17 | Q6 | H | H | Q3 | Me | — | Q38 | CH$_2$ | CH$_2$ | Q10 | Q6 | H | H | Q3 | Me |
| CH$_2$ | Q36 | CH$_2$ | CH$_2$ | Q17 | Q6 | H | H | Q3 | Me | CH$_2$ | Q38 | CH$_2$ | CH$_2$ | Q10 | Q6 | H | H | Q3 | Me |
| — | Q32 | CH$_2$ | CH$_2$ | Q18 | Q6 | H | H | Q3 | Me | — | Q39 | CH$_2$ | CH$_2$ | Q10 | Q6 | H | H | Q3 | Me |
| CH$_2$ | Q32 | CH$_2$ | CH$_2$ | Q18 | Q6 | H | H | Q3 | Me | CH$_2$ | Q39 | CH$_2$ | CH$_2$ | Q10 | Q6 | H | H | Q3 | Me |
| — | Q36 | CH$_2$ | CH$_2$ | Q18 | Q6 | H | H | Q3 | Me | — | Q40 | CH$_2$ | CH$_2$ | Q10 | Q6 | H | H | Q3 | Me |
| CH$_2$ | Q36 | CH$_2$ | CH$_2$ | Q18 | Q6 | H | H | Q3 | Me | CH$_2$ | Q40 | CH$_2$ | CH$_2$ | Q10 | Q6 | H | H | Q3 | Me |
| — | Q32 | CH$_2$ | CH$_2$ | Q19 | Q6 | H | H | Q3 | Me | — | Q41 | CH$_2$ | CH$_2$ | Q10 | Q6 | H | H | Q3 | Me |
| CH$_2$ | Q32 | CH$_2$ | CH$_2$ | Q19 | Q6 | H | H | Q3 | Me | CH$_2$ | Q41 | CH$_2$ | CH$_2$ | Q10 | Q6 | H | H | Q3 | Me |
| — | Q36 | CH$_2$ | CH$_2$ | Q19 | Q6 | H | H | Q3 | Me | — | Q42 | CH$_2$ | CH$_2$ | Q10 | Q6 | H | H | Q3 | Me |
| CH$_2$ | Q36 | CH$_2$ | CH$_2$ | Q19 | Q6 | H | H | Q3 | Me | CH$_2$ | Q42 | CH$_2$ | CH$_2$ | Q10 | Q6 | H | H | Q3 | Me |
| — | Q32 | CH$_2$ | CH$_2$ | Q20 | Q6 | H | H | Q3 | Me | — | Q43 | CH$_2$ | CH$_2$ | Q10 | Q6 | H | H | Q3 | Me |
| CH$_2$ | Q32 | CH$_2$ | CH$_2$ | Q20 | Q6 | H | H | Q3 | Me | CH$_2$ | Q43 | CH$_2$ | CH$_2$ | Q10 | Q6 | H | H | Q3 | Me |
| — | Q36 | CH$_2$ | CH$_2$ | Q20 | Q6 | H | H | Q3 | Me | Q32 | Q32 | CH$_2$ | CH$_2$ | Q10 | Q6 | H | H | Q3 | Me |
| CH$_2$ | Q36 | CH$_2$ | CH$_2$ | Q20 | Q6 | H | H | Q3 | Me | CHMe | Q32 | CH$_2$ | CH$_2$ | Q10 | Q6 | H | H | Q3 | Me |
| — | Q32 | CH$_2$ | CH$_2$ | Q21 | Q6 | H | H | Q3 | Me | CHMe | Q36 | CH$_2$ | CH$_2$ | Q1 | Q6 | H | H | Q3 | Me |
| CH$_2$ | Q32 | CH$_2$ | CH$_2$ | Q21 | 06 | H | H | Q3 | Me | Q32 | Q33 | CH$_2$ | CH$_2$ | Q10 | Q6 | H | H | Q3 | Me |
| — | Q36 | CH$_2$ | CH$_2$ | Q21 | Q6 | H | H | Q3 | Me | CHMe | Q33 | CH$_2$ | CH$_2$ | Q10 | Q6 | H | H | Q3 | Me |
| CH$_2$ | Q36 | CH$_2$ | CH$_2$ | Q21 | Q6 | H | H | Q3 | Me | Q32 | Q34 | CH$_2$ | CH$_2$ | Q10 | Q6 | H | H | Q3 | Me |
| — | Q32 | CH$_2$ | CH$_2$ | Q22 | Q6 | H | H | Q3 | Me | CHMe | Q34 | CH$_2$ | CH$_2$ | Q10 | Q6 | H | H | Q3 | Me |
| CH$_2$ | Q32 | CH$_2$ | CH$_2$ | Q22 | Q6 | H | H | Q3 | Me | Q32 | Q35 | CH$_2$ | CH$_2$ | Q10 | Q6 | H | H | Q3 | Me |
| — | Q36 | CH$_2$ | CH$_2$ | Q22 | Q6 | H | H | Q3 | Me | CHMe | Q35 | CH$_2$ | CH$_2$ | Q10 | Q6 | H | H | Q3 | Me |
| CH$_2$ | Q36 | CH$_2$ | CH$_2$ | Q22 | Q6 | H | H | Q3 | Me | Q32 | Q37 | CH$_2$ | CH$_2$ | Q10 | Q6 | H | H | Q3 | Me |
| — | Q32 | CH$_2$ | CH$_2$ | Q23 | Q6 | H | H | Q3 | Me | CHMe | Q37 | CH$_2$ | CH$_2$ | Q10 | Q6 | H | H | Q3 | Me |
| CH$_2$ | Q32 | CH$_2$ | CH$_2$ | Q23 | Q6 | H | H | Q3 | Me | Q32 | Q38 | CH$_2$ | CH$_2$ | Q10 | Q6 | H | H | Q3 | Me |
| — | Q36 | CH$_2$ | CH$_2$ | Q23 | Q6 | H | H | Q3 | Me | CHMe | Q38 | CH$_2$ | CH$_2$ | Q10 | Q6 | H | H | Q3 | Me |
| CH$_2$ | Q36 | CH$_2$ | CH$_2$ | Q23 | Q6 | H | H | Q3 | Me | Q32 | Q39 | CH$_2$ | CH$_2$ | Q10 | Q6 | H | H | Q3 | Me |
| — | Q32 | CH$_2$ | CH$_2$ | Q24 | Q6 | H | H | Q3 | Me | CHMe | Q39 | CH$_2$ | CH$_2$ | Q10 | Q6 | H | H | Q3 | Me |
| CH$_2$ | Q32 | CH$_2$ | CH$_2$ | Q24 | Q6 | H | H | Q3 | Me | Q32 | Q40 | CH$_2$ | CH$_2$ | Q10 | Q6 | H | H | Q3 | Me |
| — | Q36 | CH$_2$ | CH$_2$ | Q24 | Q6 | H | H | Q3 | Me | CHMe | Q40 | CH$_2$ | CH$_2$ | Q10 | Q6 | H | H | Q3 | Me |
| CH$_2$ | Q36 | CH$_2$ | CH$_2$ | Q24 | Q6 | H | H | Q3 | Me | Q32 | Q41 | CH$_2$ | CH$_2$ | Q10 | Q6 | H | H | Q3 | Me |
| — | Q32 | CH$_2$ | CH$_2$ | Q25 | Q6 | H | H | Q3 | Me | CHMe | Q41 | CH$_2$ | CH$_2$ | Q10 | Q6 | H | H | Q3 | Me |
| CH$_2$ | Q32 | CH$_2$ | CH$_2$ | Q25 | Q6 | H | H | Q3 | Me | Q32 | Q42 | CH$_2$ | CH$_2$ | Q10 | Q6 | H | H | Q3 | Me |
| — | Q36 | CH$_2$ | CH$_2$ | Q25 | Q6 | H | H | Q3 | Me | CHMe | Q42 | CH$_2$ | CH$_2$ | Q10 | Q6 | H | H | Q3 | Me |
| CH$_2$ | Q36 | CH$_2$ | CH$_2$ | Q25 | Q6 | H | H | Q3 | Me | Q32 | Q43 | CH$_2$ | CH$_2$ | Q10 | Q6 | H | H | Q3 | Me |
| — | Q32 | CH$_2$ | CH$_2$ | Q26 | Q6 | H | H | Q3 | Me | CHMe | Q43 | CH$_2$ | CH$_2$ | Q10 | Q6 | H | H | Q3 | Me |
| CH$_2$ | Q32 | CH$_2$ | CH$_2$ | Q26 | Q6 | H | H | Q3 | Me | — | Q32 | CH$_2$ | CH$_2$ | Q10 | Q6 | H | H | Q3 | Bn |
| — | Q36 | CH$_2$ | CH$_2$ | Q26 | Q6 | H | H | Q3 | Me | CH$_2$ | Q32 | CH$_2$ | CH$_2$ | Q10 | Q6 | H | H | Q3 | Bn |
| CH$_2$ | Q36 | CH$_2$ | CH$_2$ | Q26 | Q6 | H | H | Q3 | Me | — | Q36 | CH$_2$ | CH$_2$ | Q10 | Q6 | H | H | Q3 | Bn |
| — | Q32 | CH$_2$ | CH$_2$ | Q27 | Q6 | H | H | Q3 | Me | CH$_2$ | Q36 | CH$_2$ | CH$_2$ | Q10 | Q6 | H | H | Q3 | Bn |
| CH$_2$ | Q32 | CH$_2$ | CH$_2$ | Q27 | Q6 | H | H | Q3 | Me | — | Q32 | Q32 | CH$_2$ | Q10 | Q6 | H | H | Q3 | Me |
| — | Q36 | CH$_2$ | CH$_2$ | Q27 | Q6 | H | H | Q3 | Me | CH$_2$ | Q32 | Q32 | CH$_2$ | Q10 | Q6 | H | H | Q3 | Me |
| CH$_2$ | Q36 | CH$_2$ | CH$_2$ | Q27 | Q6 | H | H | Q3 | Me | — | Q36 | Q32 | CH$_2$ | Q10 | Q6 | H | H | Q3 | Me |
| — | Q32 | CH$_2$ | CH$_2$ | Q28 | Q6 | H | H | Q3 | Me | CH$_2$ | Q36 | Q32 | CH$_2$ | Q10 | Q6 | H | H | Q3 | Me |
| CH$_2$ | Q32 | CH$_2$ | CH$_2$ | Q28 | Q6 | H | H | Q3 | Me | | | | | | | | | | |

TABLE 1-continued

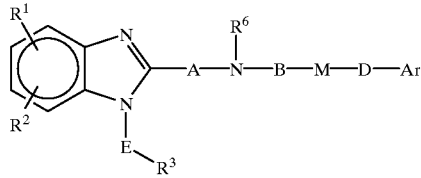

(Ia)

| A | B | D | E | M | Ar | R¹ | R² | R³ | R⁶ |
|---|---|---|---|---|---|---|---|---|---|
| — | Q32 | CH₂ | Q32 | Q10 | Q6 | H | H | OMe | Me |
| CH₂ | Q32 | CH₂ | Q32 | Q10 | Q6 | H | H | OMe | Me |
| — | Q36 | CH₂ | Q32 | Q10 | Q6 | H | H | Ome | Me |
| CH₂ | Q36 | CH₂ | Q32 | Q10 | Q6 | H | H | OMe | Me |
| — | Q32 | CH₂ | Q32 | Q10 | Q6 | H | H | OEt | Me |
| CH₂ | Q32 | CH₂ | Q32 | Q10 | Q6 | H | H | OEt | Me |
| — | Q36 | CH₂ | Q32 | Q10 | Q6 | H | H | OEt | Me |
| CH₂ | Q36 | CH₂ | Q32 | Q10 | Q6 | H | H | OEt | Me |
| — | Q32 | CH₂ | CH₂ | Q10 | Q6 | 5-F | H | Q3 | Me |
| CH₂ | Q32 | CH₂ | CH₂ | Q10 | Q6 | 5-F | H | Q3 | Me |
| — | Q36 | CH₂ | CH₂ | Q10 | Q6 | 5-F | H | Q3 | Me |
| CH₂ | Q36 | CH₂ | CH₂ | Q10 | Q6 | 5-F | H | Q3 | Me |
| — | Q32 | CH₂ | CH₂ | Q10 | Q6 | 6-F | H | Q3 | Me |
| CH₂ | Q32 | CH₂ | CH₂ | Q10 | Q6 | 6-F | H | Q3 | Me |
| — | Q36 | CH₂ | CH₂ | Q10 | Q6 | 6-F | H | Q3 | Me |
| CH₂ | Q36 | CH₂ | CH₂ | Q10 | Q6 | 6-F | H | Q3 | Me |
| — | Q32 | CH₂ | CH₂ | Q10 | Q6 | 5-Cl | H | Q3 | Me |
| CH₂ | Q32 | CH₂ | CH₂ | Q10 | Q6 | 5-Cl | H | Q3 | Me |
| — | Q36 | CH₂ | CH₂ | Q10 | Q6 | 5-Cl | H | Q3 | Me |
| CH₂ | Q36 | CH₂ | CH₂ | Q10 | Q6 | 5-Cl | H | Q3 | Me |
| — | Q32 | CH₂ | CH₂ | Q10 | Q6 | 6-Cl | H | Q3 | Me |
| CH₂ | Q32 | CH₂ | CH₂ | Q10 | Q6 | 6-Cl | H | Q3 | Me |
| — | Q36 | CH₂ | CH₂ | Q10 | Q6 | 6-Cl | H | Q3 | Me |
| CH₂ | Q36 | CH₂ | CH₂ | Q10 | Q6 | 6-Cl | H | Q3 | Me |
| — | Q32 | CH₂ | CH₂ | Q10 | Q6 | 5-Br | H | Q3 | Me |
| CH₂ | Q32 | CH₂ | CH₂ | Q10 | Q6 | 5-Br | H | Q3 | Me |
| — | Q36 | CH₂ | CH₂ | Q10 | Q6 | 5-Br | H | Q3 | Me |
| CH₂ | Q36 | CH₂ | CH₂ | Q10 | Q6 | 5-Br | H | Q3 | Me |
| — | Q32 | CH₂ | CH₂ | Q10 | Q6 | 6-Br | H | Q3 | Me |
| CH₂ | Q32 | CH₂ | CH₂ | Q10 | Q6 | 6-Br | H | Q3 | Me |
| — | Q36 | CH₂ | CH₂ | Q10 | Q6 | 6-Br | H | Q3 | Me |
| CH₂ | Q36 | CH₂ | CH₂ | Q10 | Q6 | 6-Br | H | Q3 | Me |
| — | Q32 | CH₂ | CH₂ | Q10 | Q6 | 5-F | 6-F | Q3 | Me |
| CH₂ | Q32 | CH₂ | CH₂ | Q10 | Q6 | 5-F | 6-F | Q3 | Me |
| — | Q36 | CH₂ | CH₂ | Q10 | Q6 | 5-F | 6-F | Q3 | Me |
| CH₂ | Q36 | CH₂ | CH₂ | Q10 | Q6 | 5-F | 6-F | Q3 | Me |
| — | Q32 | CH₂ | CH₂ | Q10 | Q6 | 5-Cl | 6-Cl | Q3 | Me |
| CH₂ | Q32 | CH₂ | CH₂ | Q10 | Q6 | 5-Cl | 6-Cl | Q3 | Me |
| — | Q36 | CH₂ | CH₂ | Q10 | Q6 | 5-Cl | 6-Cl | Q3 | Me |
| CH₂ | Q36 | CH₂ | CH₂ | Q10 | Q6 | 5-Cl | 6-Cl | Q3 | Me |
| — | Q32 | CH₂ | CH₂ | Q10 | Q6 | 5-Br | 6-Br | Q3 | Me |
| CH₂ | Q32 | CH₂ | CH₂ | Q10 | Q6 | 5-Br | 6-Br | Q3 | Me |
| — | Q36 | CH₂ | CH₂ | Q10 | Q6 | 5-Br | 6-Br | Q3 | Me |
| CH₂ | Q36 | CH₂ | CH₂ | Q10 | Q6 | 5-Br | 6-Br | Q3 | Me |
| — | Q32 | CH₂ | CH₂ | Q10 | Q6 | 5-Me | H | Q3 | Me |
| CH₂ | Q32 | CH₂ | CH₂ | Q10 | Q6 | 5-Me | H | Q3 | Me |
| — | Q36 | CH₂ | CH₂ | Q10 | Q6 | 5-Me | H | Q3 | Me |
| CH₂ | Q36 | CH₂ | CH₂ | Q10 | Q6 | 5-Me | H | Q3 | Me |
| — | Q32 | CH₂ | CH₂ | Q10 | Q6 | 6-Me | H | Q3 | Me |
| CH₂ | Q32 | CH₂ | CH₂ | Q10 | Q6 | 6-Me | H | Q3 | Me |
| — | Q36 | CH₂ | CH₂ | Q10 | Q6 | 6-Me | H | Q3 | Me |
| CH₂ | Q36 | CH₂ | CH₂ | Q10 | Q6 | 6-Me | H | Q3 | Me |
| — | Q32 | CH₂ | CH₂ | Q10 | Q6 | 5-OMe | H | Q3 | Me |
| CH₂ | Q32 | CH₂ | CH₂ | Q10 | Q6 | 5-OMe | H | Q3 | Me |
| — | Q36 | CH₂ | CH₂ | Q10 | Q6 | 5-OMe | H | Q3 | Me |
| CH₂ | Q36 | CH₂ | CH₂ | Q10 | Q6 | 5-OMe | H | Q3 | Me |
| — | Q32 | CH₂ | CH₂ | Q10 | Q6 | 6-OMe | H | Q3 | Me |
| CH₂ | Q32 | CH₂ | CH₂ | Q10 | Q6 | 6-OMe | H | Q3 | Me |
| — | Q36 | CH₂ | CH₂ | Q10 | Q6 | 6-OMe | H | Q3 | Me |

TABLE 1-continued

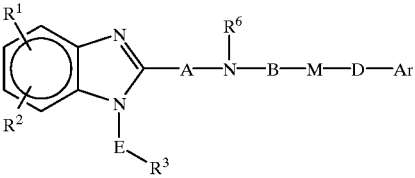

(Ia)

| A | B | D | E | M | Ar | R¹ | R² | R³ | R⁶ |
|---|---|---|---|---|---|---|---|---|---|
| CH₂ | Q36 | CH₂ | CH₂ | Q10 | Q6 | 6-OMe | H | Q3 | Me |
| — | Q32 | CH₂ | CH₂ | Q10 | Q6 | 5-Me | 6-Me | Q3 | Me |
| CH₂ | Q32 | CH₂ | CH₂ | Q10 | Q6 | 5-Me | 6-Me | Q3 | Me |
| — | Q36 | CH₂ | CH₂ | Q10 | Q6 | 5-Me | 6-Me | Q3 | Me |
| CH₂ | Q36 | CH₂ | CH₂ | Q10 | Q6 | 5-Me | 6-Me | Q3 | Me |
| — | Q32 | CH₂ | CH₂ | Q10 | Q6 | 5-OMe | 6-OMe | Q3 | Me |
| CH₂ | Q32 | CH₂ | CH₂ | Q10 | Q6 | 5-OMe | 6-OMe | Q3 | Me |
| — | Q36 | CH₂ | CH₂ | Q10 | Q6 | 5-OMe | 6-OMe | Q3 | Me |
| CH₂ | Q36 | CH₂ | CH₂ | Q10 | Q6 | 5-OMe | 6-OMe | Q3 | Me |

The compound of the formula (I) of the present invention can be used for the purpose of the present invention either in its free form or in the form of a pharmacologically acceptable salt. Such an acid addition salt may, for example, be a mineral acid salt (such as a hydrochloride, a hydrobromide, a sulfate, a hydrogen sulfate, a nitrate, a phosphate, a hydrogen phosphate or a dihydrogen phosphate), an organic acid salt (such as a formate, an acetate, a propionate, a succinate, a malonate, an oxalate, a maleate, a fumarate, a malate, a citrate, a tartarate, a lactate, a glutamate, an asparatate, a picrate or a carbonate), or a sulfonate (such as a methanesulfonate, a benzenesulfonate or a toluenesulfonate).

Now, processes for the production of the compounds of the present invention will be described.

The benzimidazole derivatives of the formula (I) as the compounds of the present invention can be produced by processes represented by the following reaction schemes (1) to (7).

Reaction scheme (1)

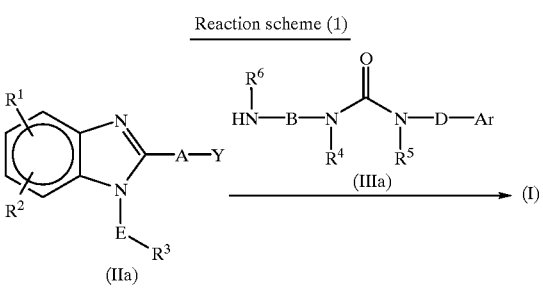

wherein A, B, D, E, X, Ar, X, R¹, R², R³, R⁴, R⁵ and R⁶ are as defined above, and Y is a leaving group such as a halogen atom such as a chlorine atom, a bromine atom or an iodine atom, a methanesulfonyloxy group, a p-toluenesulfonyloxy group, or a trifluoromethanesulfonyloxy group.

The reaction scheme (1) is a process for producing the compound of the present invention by reacting a compound (IIa) with a compound (IIIa).

This reaction is carried out usually in the presence or absence of an inorganic base or an organic base.

The inorganic base includes metal carbonates such as potassium carbonate, sodium carbonated, lithium carbonate, potassium bicarbonate and sodium bicarbonate, metal hydroxides such as lithium hydroxide, sodium hydroxide and potassium hydroxide, metal hydrides such as sodium hydride, potassium hydride and n-butyl lithium, metal alkoxides such as sodium methoxide, sodium ethoxide and potassium t-butoxide, and metal amides such as sodium amide, lithium diisopropylamide, lithium hexamethyldisilazide, sodium hexamethyldisilazide and 2,2,6,6-tetramethylpiperidide.

The organic base includes, for example, trimethylamine, triethylamine, pyridine and diisopropylethylamine.

The solvent for the reaction may be any solvent so long as it will not be involved in the reaction, and it may, for example, be a hydrocarbon type solvent such as benzene, toluene or hexane, an ether type solvent such as tetrahydrofuran, diethyl ether or 1,4-dioxane, an amide type solvent such as formamide, N,N-dimethylacetamide, N,N-dimethylformamide or N-methylpyrrolidone, an alcohol type solvent such as methanol, ethanol or propanol, a halogen type solvent such as chloroform, methylene chloride or ethylene chloride, other solvent such as acetonitrile or dimethylsulfoxide, water, or a solvent mixture thereof. However, the reaction may be carried out in the absence of a solvent.

The temperature for the reaction may be within a range of from −78° C. to the boiling point of the solvent used for the reaction.

The molar ratio of the starting materials can optionally be set, but the compound (IIIa) may be used in an amount of from 0.8 to 10 mols per mol of the compound (IIa).

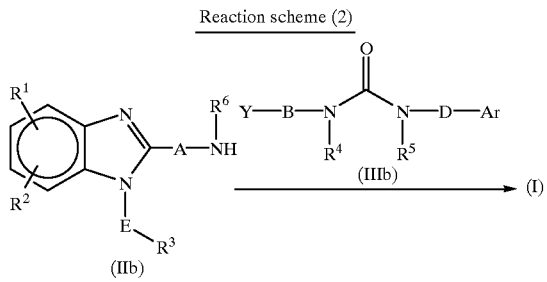

wherein A, B, D, E, X, Y, Ar, $R^1$, $R^2$, $R^3$, $R^4$, $R^5$ and $R^6$ are as defined above.

The reaction scheme (2) is a process for producing the compound of the present invention by reacting a compound (IIb) with a compound (IIIb).

This reaction can be carried out under conditions similar to reaction scheme (1).

The molar ratio of the starting materials can optionally be set, but the compound (IIb) may be used in an amount of from 0.8 to 10 mols per mol of the compound (IIIb).

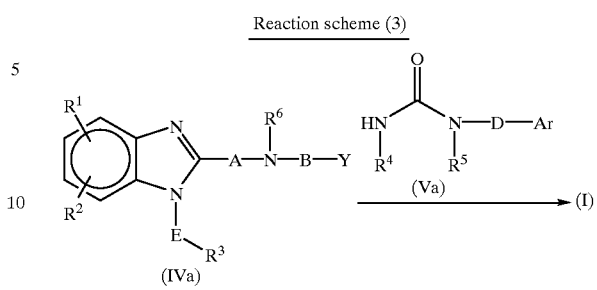

wherein A, B, D, E, X, Y, Ar, $R^1$, $R^2$, $R^3$, $R^4$, $R^5$ and $R^6$ are as defined above.

The reaction scheme (3) is a process for producing the compound (I) of the present invention by reacting a compound (IVa) with a compound (Va).

This reaction can be carried out under conditions similar to the reaction scheme (1).

The molar ratio of the starting materials may be optionally set, but the compound (Va) may be used in an amount of from 0.8 to 1.5 mols per mol of the compound (IVa).

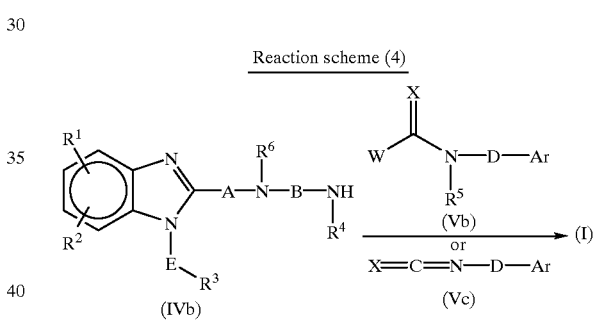

wherein A, B, D, E, X, Ar, $R^1$, $R^2$, $R^3$, $R^4$, $R^5$ and $R^6$ are as defined above, and W is a halogen atom such as a chlorine atom, a bromine atom or an iodine atom, an alkyl(aryl)thio group such as a methylthio group, a benzylthio group or a phenylthio group, or an alkyl(aryl)oxy group such as a methoxy group, a benzyloxy group or a phenyloxy group.

The reaction scheme (4) is a process for producing the compound (I) of the present invention by reacting the compound (IVb) with a compound (Vb) or a compound (Vc). (When the compound (Vc) is employed, $R^5$ in the compound (I) will be a hydrogen atom.)

This reaction can be accomplished by heating or cooling the compound (IVb) and the compound (Vb) or the compound (IVb) and the compound (Vc), in a solvent or in the absence of a solvent, and may be carried out under conditions similar to the reaction scheme (1).

The molar ratio of the starting materials may optionally be set, but the compound (Vb) or the compound (Vc) may be used in an amount of from 0.8 to 1.5 mols per mol of the compound (IVb).

Reaction scheme (5)

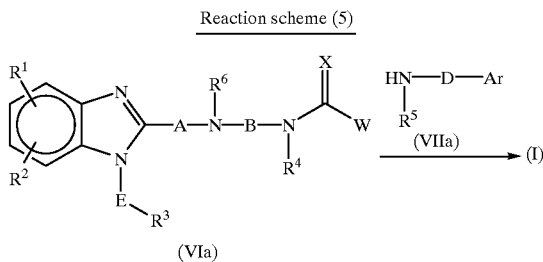

wherein A, B, D, E, X, W, Ar, $R^1$, $R^2$, $R^3$, $R^4$, $R^5$ and $R^6$ are as defined above.

The reaction scheme (5) is a process for producing the compound (I) of the present invention by reacting a compound (VIa) with a compound (VIIa).

This reaction can be accomplished by heating or cooling the compound (VIa) and the compound (VIIa) in a solvent or in the absence of a solvent, and may be carried out under conditions similar to the reaction scheme (1).

The molar ratio of the starting materials may optionally be set, but the compound (VIa) may be used in an amount of from 0.8 to 1.5 mols per mol of the compound (VIIa).

Reaction scheme (6)

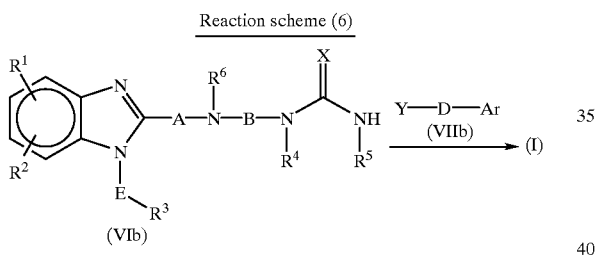

wherein A, B, D, E, X, Y, Ar, $R^1$, $R^2$, $R^3$, $R^4$, $R^5$ and $R^6$ are as defined above.

The reaction scheme (6) is a process for producing the compound (I) of the present invention by reacting a compound (VIb) with a compound (VIIb).

This reaction can be carried out under conditions similar to the reaction scheme (1).

The molar ratio of the starting materials may optionally be set, but the compound (VIb) may be used in an amount of from 0.8 to 1.5 mols per mol of the compound (VIIb).

Reaction scheme (7)

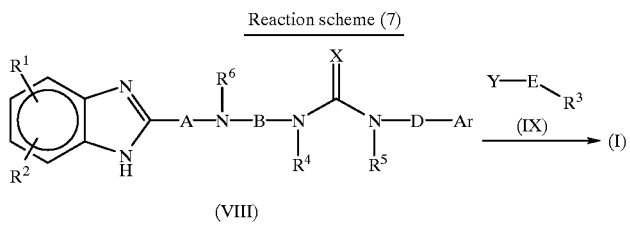

wherein A, B, D, E, X, Y, Ar, $R^1$, $R^2$, $R^3$, $R^4$, $R^5$ and $R^6$ are as defined above.

The reaction scheme (7) is a process for producing the compound (I) of the present invention by reacting a compound (VIII) with a compound (IX).

This reaction can be carried out under conditions similar to the reaction scheme (1).

The molar ratio of the starting materials may optionally be set, but the compound (IX) may be used in an amount of from 0.8 to 1.5 mols per mol of the compound (VIII).

Now, processes for producing starting materials for the compounds of the present invention will be described.

Among the starting materials for the compounds of the present invention, the compound (IIa) and the compound (IIb) can be produced by the processes shown by the reaction scheme (8).

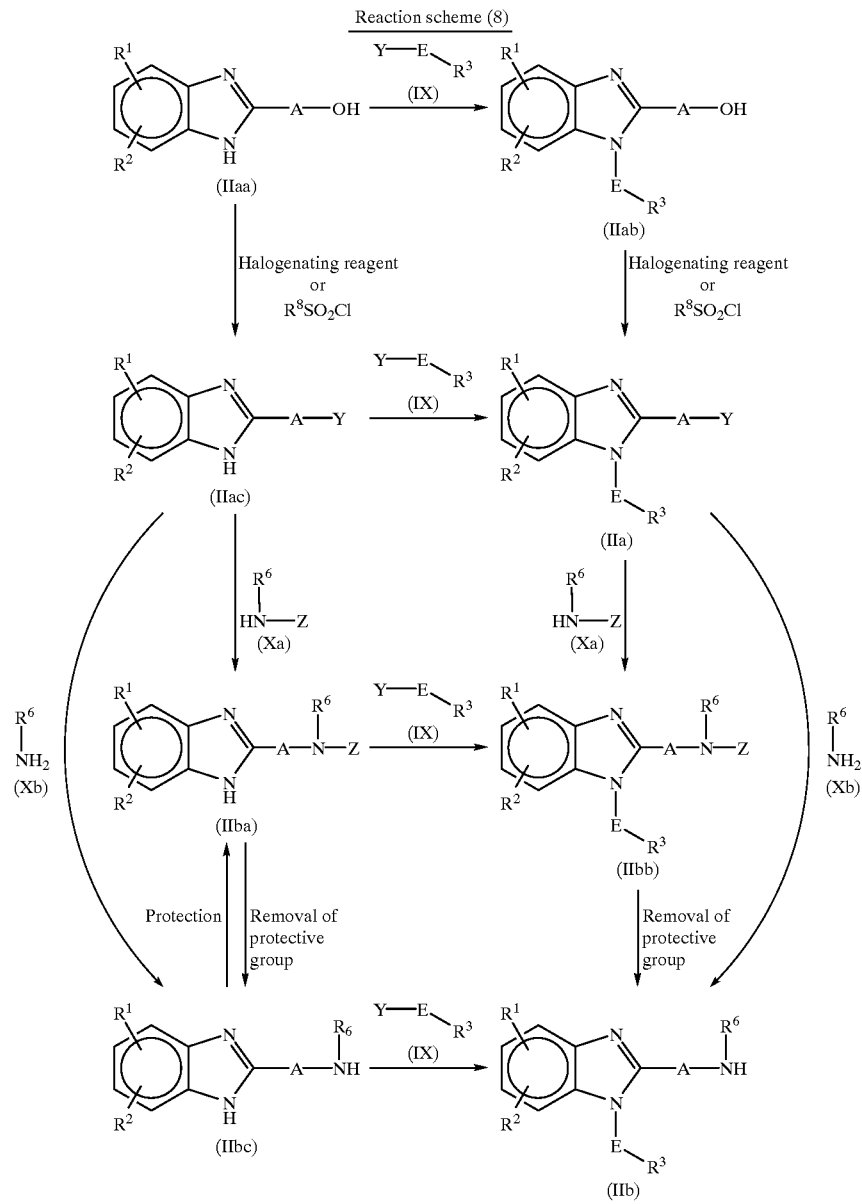

wherein A, E, Y, $R^1$, $R^2$, $R^3$ and $R^6$ are as defined above, $R^8$ is, for example, a methyl group, a trifluoromethyl group, a phenyl group or a 4-methylphenyl group, and Z is a protective group for an amino group, such as a formyl group, an acetyl group, a benzyloxycarbonyl group or a t-butoxycarbonyl group.

The compound (IIa) can be produced by condensing the compound (IIaa) with the compound (IX) to obtain the compound (IIab), followed by halogenation (the halogenating reagent may be a chlorinating reagent such as phosphorus pentachloride, thionyl chloride, sulfuryl chloride, chlorine-triphenylphosphine or carbon tetrachloride-triphenylphosphine, a brominating reagent such as phosphorus tribromide, phosphorus pentabromide, thionyl bromide, sulfuryl bromide, bromine-triphenylphosphine or carbon tetrabromide-triphenylphosphine), or reacting it with $R^8SO_2Cl$, or by halogenating the compound (IIaa) or reacting it with $R^8SO_2Cl$ to obtain a compound (IIac), followed by condensing it with the compound (IX).

The compound (IIb) can be produced by reacting the compound (IIa) with the compound (Xb) or reacting the compound (IIa) with the compound (Xa) to obtain the compound (IIbb), followed by removal of the protective group, or by reacting the compound (IIac) with the compound (Xa) to obtain the compound (IIba), followed by reacting it with the compound (IX) to obtain the compound (IIbb), followed by removal of the protective group, or conducting the removal of the protective group first to obtain the compound (IIbc), followed by reacting it with the compound (IX), or by reacting the compound (IIac) with the compound (Xb) to obtain the compound (IIbc), followed by reacting it with the compound (IX) or protecting it to obtain the compound (IIba), followed by reacting it with the compound (IX) to obtain the compound (IIbb), followed by removal of the protective group.

Among the starting materials for the compounds of the present invention, the compound (IVa) can be produced by the processes shown by the reaction scheme (9).

Reaction scheme (9)

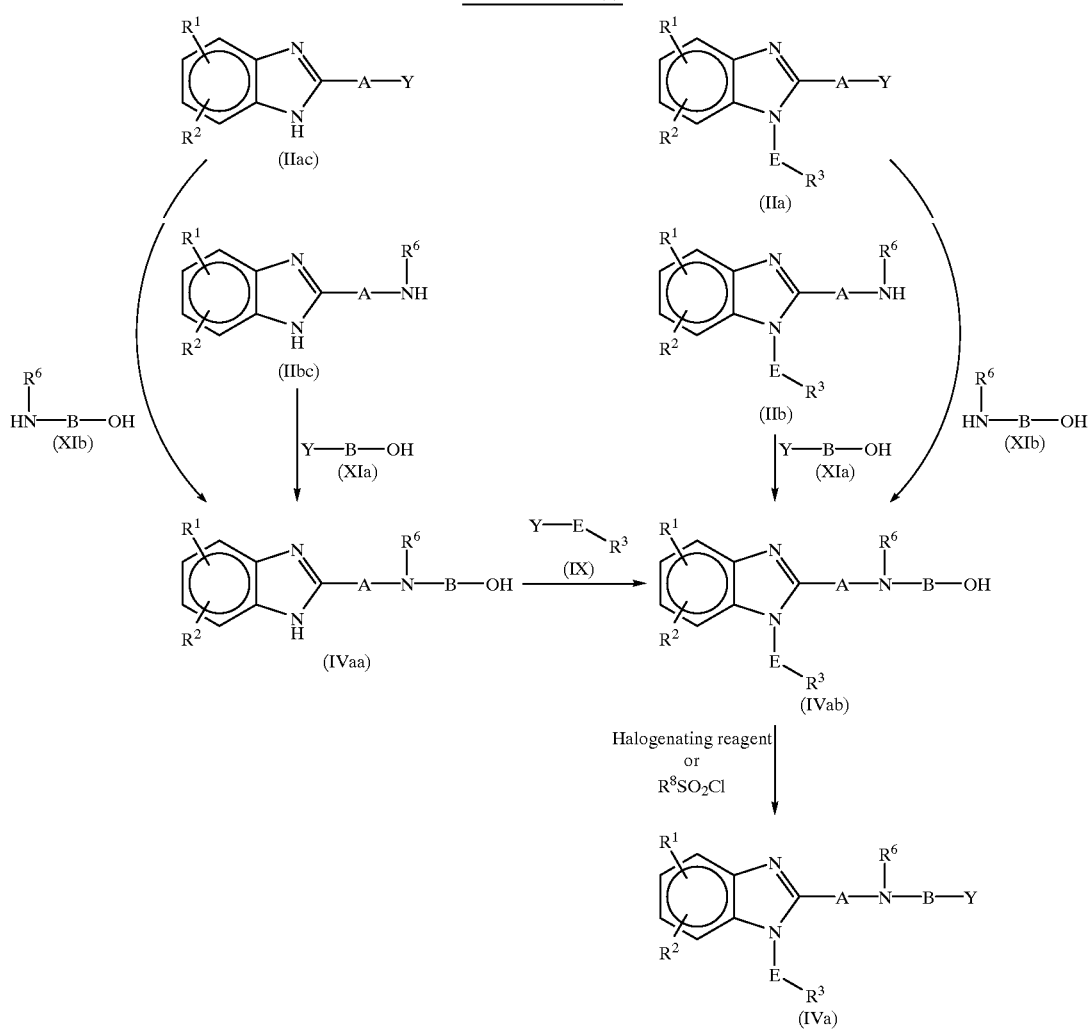

wherein A, B, E, Y, $R^1$, $R^2$, $R^3$, $R^6$ and $R^8$ are as defined above.

The compound (IVa) can be produced by reacting the compound (IIa) with the compound (XIb) or reacting the compound (IIb) with the compound (XIa) to obtain the compound (IVab), followed by halogenating it or reacting it with $R^8SO_2Cl$, or by reacting the compound (IIac) with the compound (XIb) or reacting the compound (IIbc) with the compound (XIa) to obtain the compound (IVaa), followed by reacting it with the compound (IX) to obtain the compound (IVab), followed by halogenating it or reacting it with $R^8SO_2Cl$.

Among the starting materials for the compounds of the present invention, the compound (IVb) can be produced by the processes shown by the reaction scheme (10).

Reaction scheme (10)

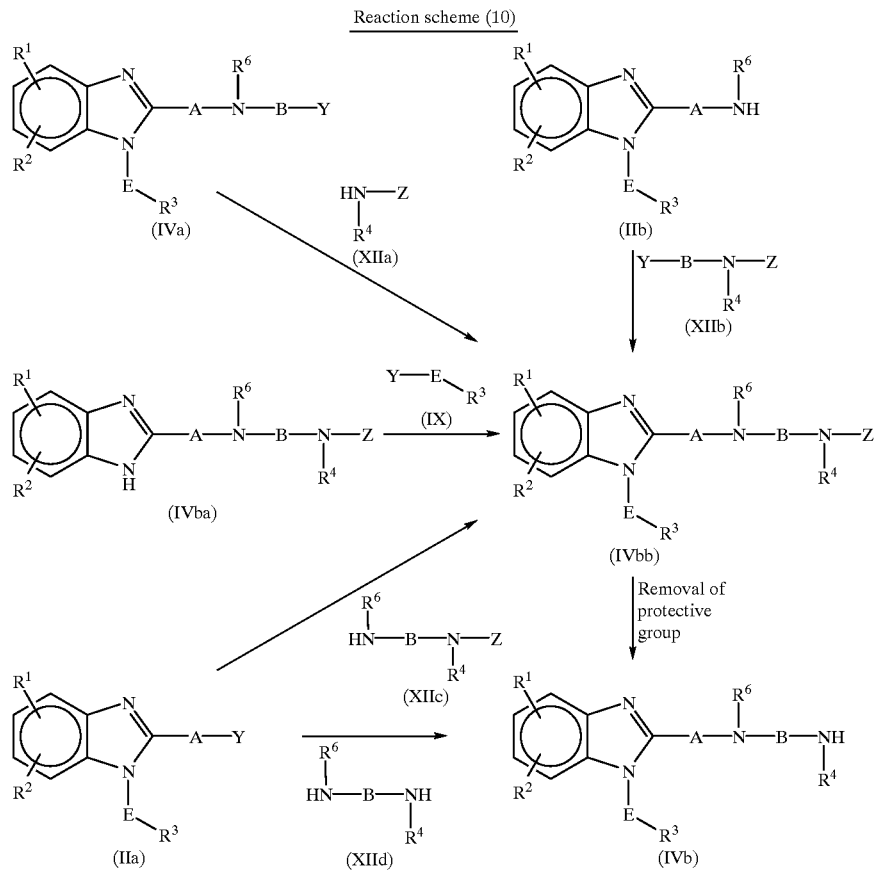

wherein A, B, E, Y, Z, $R^1$, $R^2$, $R^3$, $R^4$ and $R^6$ are as defined above.

The compound (IVb) can be produced by removing the protective group of the compound (IVbb) or reacting the compound (IIa) with the compound (XIId). The intermediate (IVbb) can be produced by reacting the compound (IIb) with the compound (XIIb), reacting the compound (IVa) with the compound (XIIa), reacting the compound (IVba) with the compound (IX), or reacting the compound (IIa) with the compound (XIIc).

Among the starting materials for the compounds of the present invention, the compound (VIa) can be produced by the processes shown by the reaction scheme (11).

Reaction scheme (11)

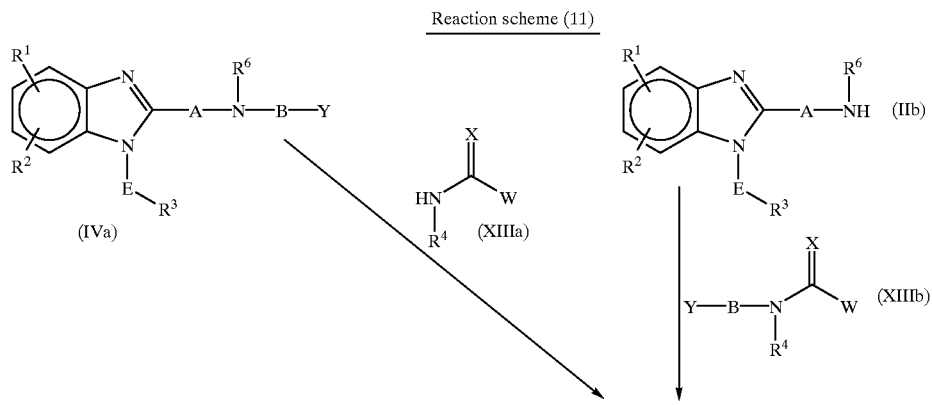

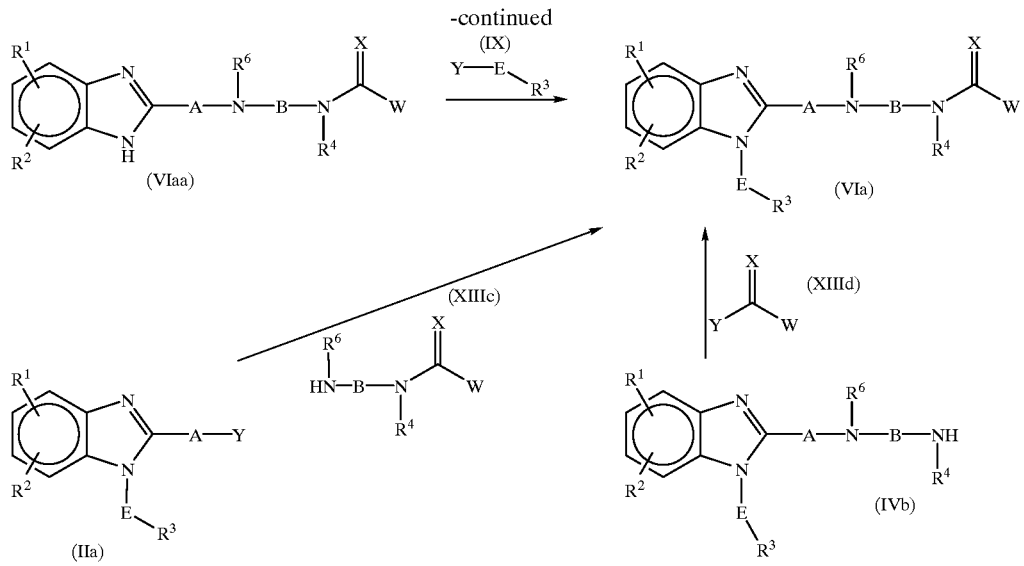

wherein A, B, E, X, Y, W, $R^1$, $R^2$, $R^3$, $R^4$ and $R^6$ are as defined above.

The compound (VIa) can be produced by reacting the compound (IIb) with the compound (XIIIb), reacting the compound (IVa) with the compound (XIIIa), reacting the compound (VIaa) with the compound (IX), reacting the compound (IIa) with the compound (XIIIc), or reacting the compound (IVb) with the compound (XIIId).

Among the starting materials for the compounds of the present invention, the compound (VIb) can be produced by the processes shown by the reaction scheme (12).

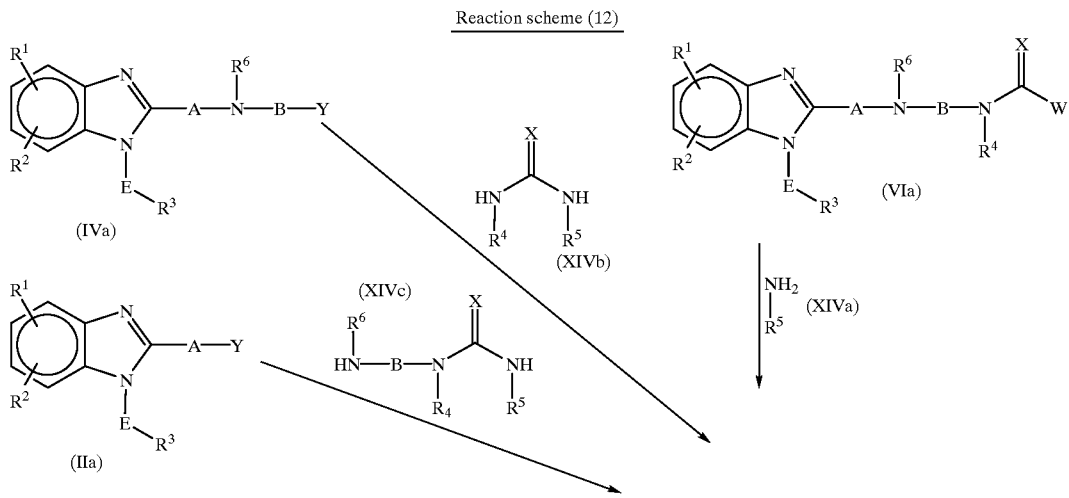

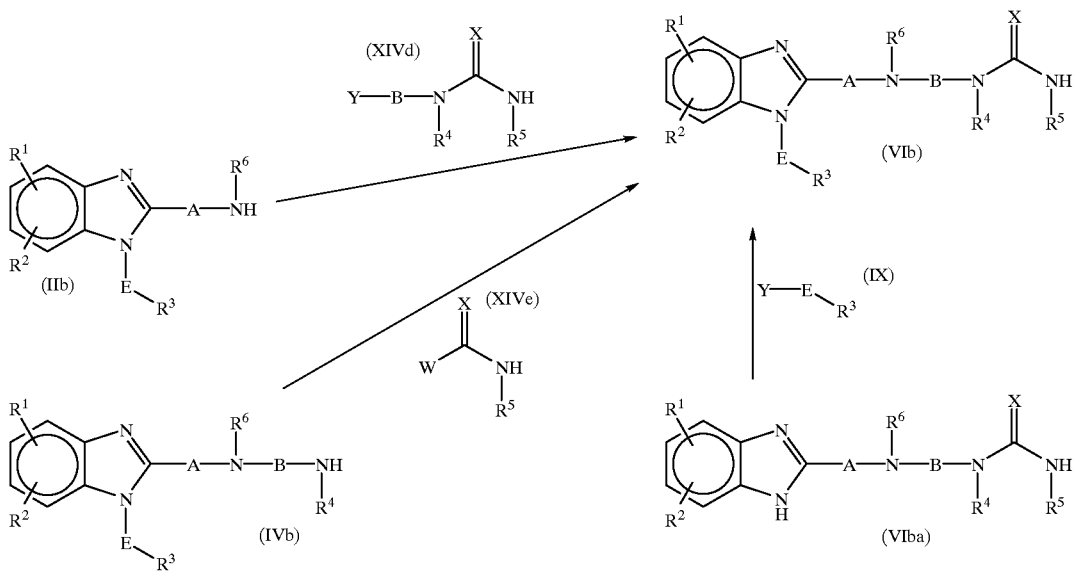

wherein A, B, E, X, Y, W, $R^1$, $R^2$, $R^3$, $R^4$, $R^5$ and $R^6$ are as defined above.

The compound (VIb) can be produced by reacting the compound (VIa) with the compound (XIVa), reacting the compound (IVa) with the compound (XIVb), reacting the compound (IIa) with the compound (XIVc), reacting the compound (IIb) with the compound (XIVd), reacting the compound (IVb) with the compound (XIVe), or reacting the compound (IVba) with the compound (IX).

Among the starting materials for the compounds of the present invention, the compound (VIII) can be produced by the processes shown by the reaction scheme (13).

Reaction scheme (13)

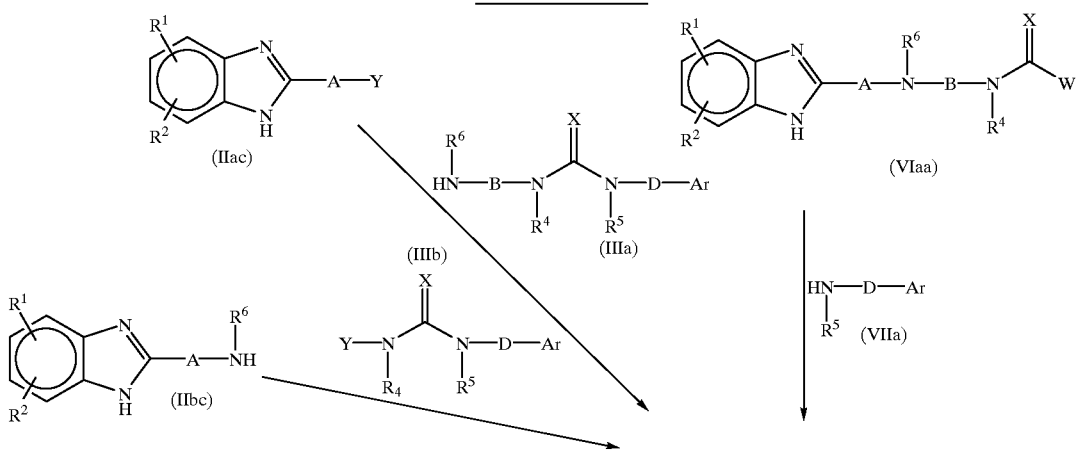

-continued

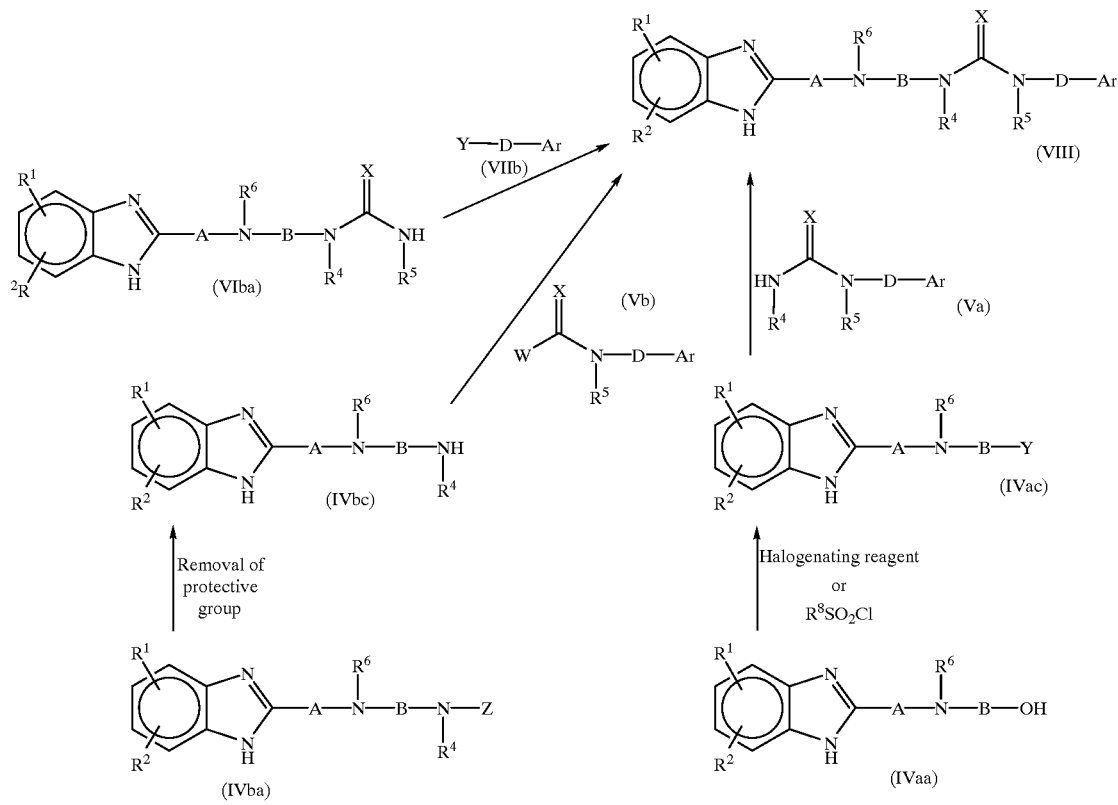

wherein A, B, D, X, Y, W, Ar, $R^1$, $R^2$, $R^3$, $R^4$, $R^5$, $R^6$ and $R^8$ are as defined above.

The compound (VIII) can be produced by reacting the compound (VIaa) with the compound (VIIa), reacting the compound (IIac) with the compound (IIIa), reacting the compound (VIba) with the compound (VIIb), reacting the compound (IIbc) with the compound (IIIb), removing the protective group of the compound (IVba) to obtain the compound (IVbc), followed by reacting it with the compound (Vb), or halogenating the compound (IVaa) or reacting it with $R^8SO_2Cl$ to obtain the compound (IVac), followed by reacting it with the compound (Va).

The reactions of the following compounds disclosed in the reaction schemes (8) to (13), i.e. (VIaa) and (VIIa), (IIac) and (IIIa), (IIbc) and (IIIb), (VIba) and (VIIb), (IVbc) and (Vb), (IVac) and (Va), (IVb) and (XIVe), (IIb) and (XIVd), (IIa) and (XIVc), (VIa) and (XIVa), (IVa) and (XIVb), (IVa) and (XIIIa), (IIb) and (XIIIb), (IIa) and (XIIIc), (IVb) and (XIIId), (IIac) and (XIb), (IIa) and (XIb), (IIbc) and (XIa), (IIb) and (XIa), (IIb) and (XIIb), (IVa) and (XIIa), (IIa) and (XIIc), (IIa) and (XIId), (IIac) and (Xa), (IIa) and (Xa), (IIac) and (Xb), (IIa) and (Xb), (VIaa) and (IX), (VIba) and (IX), (IVba) and (IX), (IVaa) and (IX), (IIaa) and (IX), (IIac) and (IX), (IIba) and (IX), and (IIbc) and (IX), can be carried out under conditions similar to the reaction scheme (1). The reactions may be carried out also in the absence of a solvent. The molar ratios of the compounds may be optionally set, but they may be within a range of from 0.1:1 to 1:0.1.

The intermediates (IVba), (IVbc), (VIaa) and (VIba) disclosed in the reaction schemes (10) to (13) can be produced by the processes shown by the reaction schemes (14) to (16).

Reaction Scheme (14)

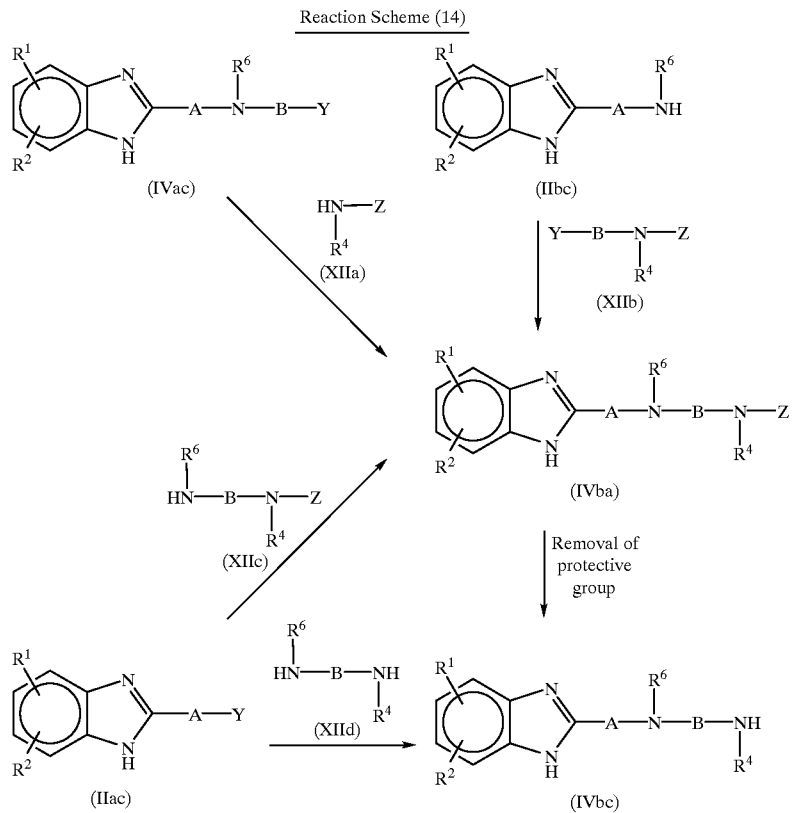

wherein A, B, Y, Z, $R^1$, $R^2$, $R^4$ and $R^6$ are as defined above.

The compound (IVba) can be produced by reacting the compound (IIbc) with the compound (XIIb), reacting the compound (IVac) with the compound (XIIa), or reacting the compound (IIac) with the compound (XIIc).

The compound (IVbc) can be produced by reacting the compound (IIac) with the compound (XIId), or by reacting the compound (IIac) with the compound (XIIc) to obtain the compound (IVba), followed by removing the protective group.

Reaction Scheme (15)
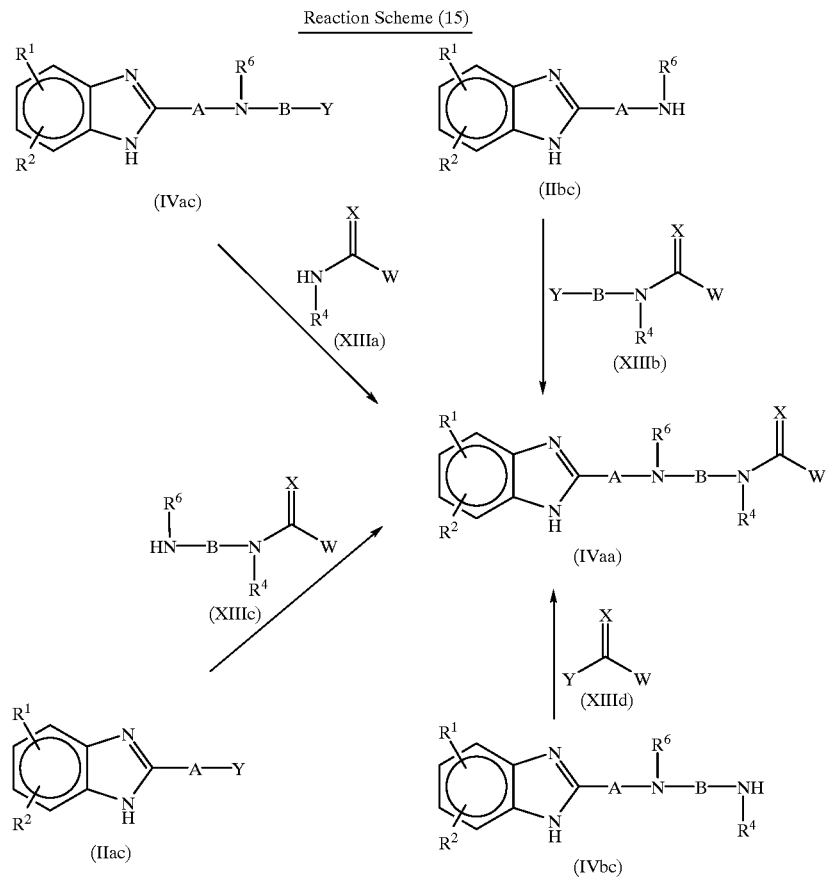
wherein A, B, X, Y, W, $R^1$, $R^2$, $R^4$ and $R^6$ are as defined above.
The compound (VIaa) can be produced by reacting the compound (IIbc) with the compound (XIIIb), reacting the compound (IVac) with the compound (XIIIa), reacting the compound (IIac) with the compound (XIIIc), or reacting the compound (IVbc) with the compound (XIIId).

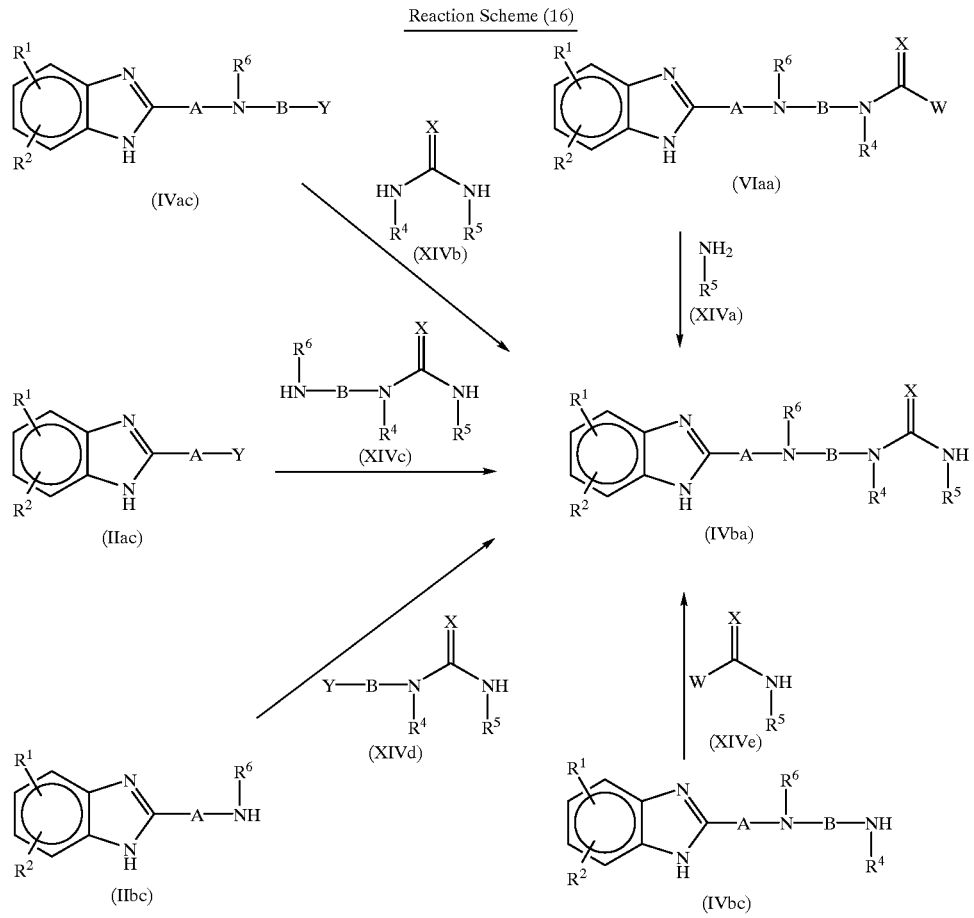

Reaction Scheme (16)

wherein A, B, X, Y, W, $R^1$, $R^2$, $R^4$, $R^5$ and $R^6$ are as defined above.

The compound (VIba) can be produced by reacting the compound (VIaa) with the compound (XIVa), reacting the compound (IVac) with the compound (XIVb), reacting the compound (IIac) with the compound (XIVc), reacting the compound (IIbc) with the compound (XIVd), or reacting the compound (IVbc) with the compound (XIVe).

The reactions of the following compounds disclosed in the reaction schemes (14) to (16), i.e. (IIac) and (XIIc), (IIac) and (XIId), (IIbc) and (XIIb), (IVac) and (XIIa), (IVac) and (XIIIa), (IIbc) and (XIIIb), (IIac) and (XIIIc), (IVbc) and (XIIId), (VIaa) and (XIVa), (IVac) and (XIVb), (IIac) and (XIVc), (IIbc) and (XIVd), and (IVbc) and (XIVe), can be carried out under conditions similar to the reaction scheme (1). Further, the reactions may be carried out also in the absence of a solvent. The molar ratios of the compounds can be optionally set, but they may be within a range of from 0.1:1 to 1:0.1.

The processes shown by the reaction scheme (17) may be employed as processes for producing the benzimidazole structure.

Reaction Scheme (17)

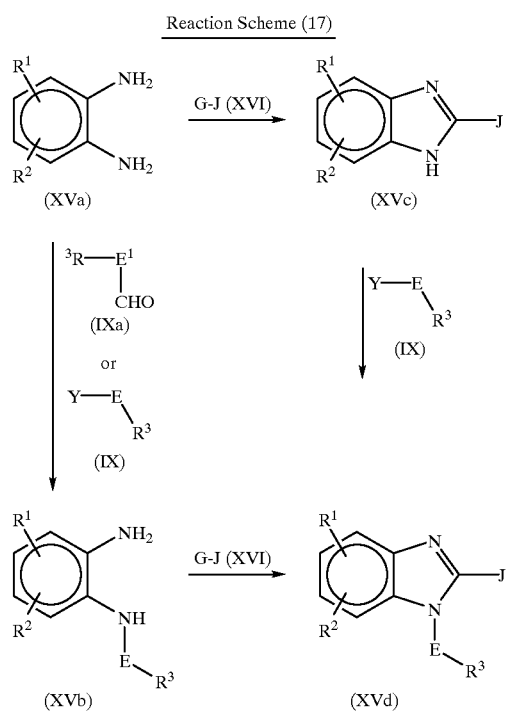

wherein E, Y, $R^1$, $R^2$ and $R^3$ are as defined above, $E^1$ is a single bond or a methylene group which may optionally be substituted by a $C_{1-4}$ alkyl group, J is AOH, AY, $ANR^6H$, $ANR^6Z$, $ANR^6BY$, $ANR^6BOH$, $ANR^6BNR^4H$, $ANR^6BNR^4Z$, $ANR^6BNR^4C(=X)W$, $ANR^6BNR^4C(=X)NR^5H$ or $ANR^6BNR^4C(=X)NR^5DAr$ (wherein A, B, D, X, Y, Z, W, Ar, $R^4$, $R^5$ and $R^6$ are as defined above), and G is COOH, COCl, COBr, $CONH_2$, $CSNH_2$, CHO, CN, $COOR^9$ (wherein $R^9$ is a $C_{1-4}$ alkyl group, a $C_{1-4}$ acyl group, a phenyl group or a benzyl group), $C(=NH)OR^{10}$, $CH(OR^{10})_2$ (wherein $R^{10}$ is a $C_{1-4}$ alkyl group, a phenyl group or a benzyl group) or $CONHNHR^9$ (wherein $R^9$ is as defined above).

The benzimidazole derivative of the formula (XVc) can be prepared by condensing the diaminobenzene derivative of the formula (XVa) with the compound (XVI). Further, the benzimidazole derivative of the formula (XVd) can be produced by condensing the diaminobenzene derivative of the formula (XVb) with the compound (XVI), or by reacting the compound (XVc) with the compound (IX). The intermediate (XVb) can be produced by reacting the compound (XVa) with the compound (IX), or by condensing the compound (IXa) under a reducing condition.

With respect to the production conditions, reference may be made to the methods disclosed in e.g. J. Org. Chem., 28, 1931 (1963); J. Chem. Soc., 2238 (1953); J. Am. Chem. Soc., 77, 5652 (1955); J. Chem. Soc., 673 (1956); J. Am. Chem. Soc., 73, 5907 (1951); J. Am. Chem. Soc., 70, 2415 (1948); J. Chem. Soc., 625, (1943); Khim. Geterotsikl. Soedin., 5, 684 (1982); J. Org. Chem., 56(6), 2260 (1991); Synth. Commnn., 16(1), 35 (1986); Khim. Geterotsikl. Soedin., 71 (1980); J. Chem. Soc. C., 20 (1967); Chim. Ther., 2, 95 (1967); J. Org. Chem., 27, 2163 (1962); Chem. Pharm. Bull., 12, 773 (1964); J. Chem. Soc., 2296 (1959); J. Am. Chem. Soc., 79, 4391 (1957); J. Chem. Soc., 1401 (1949).

By the above processes, the compounds (IIaa), (IIac), (IIbc), (IIba), (IVac), (IVaa), (IVbc), (IVba), (VIaa), (VIba) and (VIII) may be produced directly from the compound (XVa). Further, the compounds (IIab), (IIa), (IIb), (IIbb), (IVa), (IVab), (IVbb), (IVb), (VIa), (VIb) and (I) may be produced directly from the compound (XVb).

For the production of the compounds (XVa) and (XVb), the processes shown in the reaction scheme (18) may be employed.

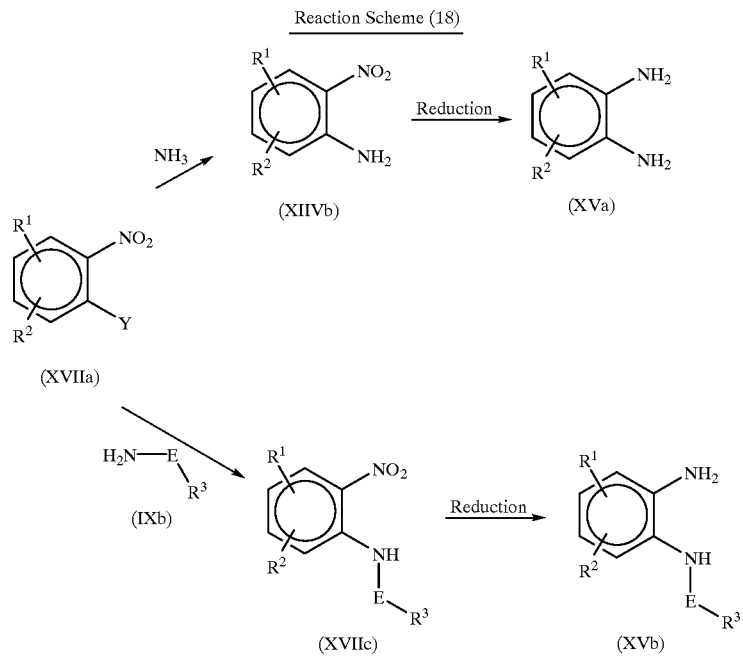

Reaction Scheme (18)

wherein E, Y, $R^1$, $R^2$ and $R^3$ are as defined above.

The compound (XVa) can be produced by reacting the compound (XVIIa) with ammonia to obtain the compound (XVIIb), followed by reducing it. Further, the compound (XVb) can be produced by reacting the compound (XVIIa) with the compound (IXb) to obtain the compound (XVIIc), followed by reducing it.

As described in the foregoing, the present inventors have found that the compound of the formula (I) of the present invention is a superior compound as a strong antiallergic agent, and it is not only useful as an active ingredient for a preventive or curing agent for pollinosis, urticaria, atopic dermatitis, allergic rhinitis and asthma etc., but also effective against other substance P related diseases, for example, eye diseases such as conjunctivitis and spring catarrh; inflammatory diseases such as chronic rheumatoid arthritis; pains such as migraine, headache, toothache and aches accompanying various diseases; gastrointestinal diseases such as ulcerative colitis and Crohn's disease; and mental diseases such as depression and dysthymia. Thus, the present invention provides a pharmaceutical composition containing the compound of the present invention in an amount effective for treatment of these diseases.

The mode of administration of the compound of the present invention may be parenteral administration of an injection (hypodermic, intravenous, intramuscular or intraperitoneal injection), an ointment, a suppository or an aerosol or oral administration of tablets, capsules, granules, pills, a syrup, a liquid, an emulsion or a suspension.

The pharmacological or veterinary composition containing a compound of the present invention contains the compound of the present invention in an amount of from about 0.01 to 99.5%, preferably from about 0.1 to 30%, based on the total weight of the composition.

In addition to the compound of the present invention, other pharmacological or veterinary active compound may be incorporated into the composition. Such a composition may contain a plurality of compounds of the present invention.

The effective dose of the compound of the present invention is usually from about 0.003 to 1.5 g, preferably from about 0.01 to 0.6 g, per an adult per day, although its clinical dose depends on the age, weight, sensitivity and condition of the patient. However, if necessary, the dose may be out of the above-mentioned range.

The compounds of the present invention may be formulated into various formulations suitable for administration in accordance with pharmaceutically conventional methods.

Namely, tablets, capsules, granules or pills for oral administration, may be prepared by using an excipient such as sugar, lactose, glucose, starch or mannitol; a binder such as hydroxypropylcellulose, syrup, gum arabic, gelatin, sorbitol, tragacanth gum, methylcellulose or polyvinylpyrrolidone; a disintegrant such as starch, carboxymethylcellulose or its calcium salt, microcrystalline cellulose or polyethylene glycol; a gloss agent such as talc, magnesium or calcium stearate or silica; or a lubricant such as sodium laurate or glycerol.

Injections, solutions, emulsions, suspensions, syrups or aerosols, may be prepared by using a solvent for the active ingredient such as water, ethyl alcohol, isopropyl alcohol, propylene glycol, 1,3-butylene glycol or polyethylene glycol; a surfactant such as a sorbitan fatty acid ester, a polyoxyethylene sorbitan fatty acid ester, a polyoxyethylene fatty acid ester, a polyoxyethylene ether of hydrogenated castor oil or lecithin; a suspending agent such as a cellulose derivative such as a sodium salt of carboxymethyl or methylcellulose, or a natural rubber such as tragacanth gum or gum arabic; or a preservative such as a paraoxybenzoic acid ester, benzalkonium chloride or a salt of sorbic acid.

Ointments for percutaneous absorption may be prepared by using white soft paraffin, liquid paraffin, a higher alcohol, macrogol ointment, hydrophilic ointment or an aqueous gel-type vehicle.

Suppositories may be prepared by using e.g. cacao butter, polyethylene glycol, lanolin, fatty acid triglyceride, coconut butter or polysorbate.

BEST MODE FOR CARRYING OUT THE INVENTION

EXAMPLES

Now, the present invention will be described in further detail with reference to Examples (including Preparation Examples, Formulation Examples and Test Examples). However, it should be understood that the present invention is by no means restricted by these specific Examples.

The symbol "m.p." indicates "melting point".

Reference Example 1

N-methyl-N-(benzimidazol-2-yl)-N'-methyl-N'-t-butoxycarbonyl-1,3-propylenediamine A solution comprising 1.1 g of 2-chlorobenzimidazole and 1.6 g of N,N'-dimethyl-1,3-propylenediamine was heated at a temperature of from 120 to 130° C. for two hours. After cooling, the solution was diluted with 50 ml of chloroform and washed with 30 ml of a 1 N potassium carbonate aqueous solution. It was dried over anhydrous sodium sulfate, and then the solvent was distilled under reduced pressure. The obtained residue was dissolved in 50 ml of chloroform, and 5 g of di-t-butyl dicarbonate was added thereto. The mixture was left to stand at room temperature for one hour, and then the solvent was distilled off under reduced pressure. The obtained residue was crystallized from diethyl ether to obtain 2.1 g of the above identified compound as pale brown crystals.

Reference Example 2

N-methyl-N-(benzimidazol-2-yl)-N'-methyl-N'-t-butoxycarbonyl-1,2-ethylenediamine In the same manner as in Reference Example 1, 1.1 g of the above identified compound was obtained as pale brown crystals, from 1.0 g of 2-chlorobenzimidazole and 4.0 g of N,N'-dimethyl-1,2-ethylenediamine.

Reference Example 3

N-methyl-N-(benzimidazol-2-yl)methyl-N'-methyl-N'-t-butoxycarbonyl- 1,3-propylenediamine 4.0 g of 2-chloromethylbenzimidazole was added under cooling with ice to a solution comprising 5.0 g of N,N'-dimethyl-1,3-propylenediamine and 30 ml of ethanol, and the mixture was stirred for one hour. The mixture was returned to room temperature and stirred overnight, whereupon the solvent was distilled off under reduced pressure. To the obtained residue, 50 ml of water and 50 ml of chloroform were added, and potassium carbonate was added until the mixture became basic. The organic layer was taken and dried over anhydrous potassium sulfate, and then, the solvent was distilled off under reduced pressure. To the obtained residue, 50 ml of chloroform was added, and 8 g of di-t-butyl dicarbonate was added to this solution. The mixture was stirred at room temperature for one hour, and then the solvent was distilled off under reduced pressure. The obtained residue was purified by silica gel column chromatography (eluent: ethyl acetate/ethanol=9/1) to obtain 7.0 g of the above identified compound as a brown oily substance.

Reference Example 4

N-methyl-N-(benzimidazol-2-yl)methyl-N'-methyl-N'-t-butoxycarbonyl-1,2-ethylenediamine In the same manner as in Reference Example 3, 6.5 g of the above identified compound was obtained as a orange colored oily substance from 8.0 g of N,N'-dimethyl-1,2-ethylenediamine and 5.0 g of 2-chloromethylbenzimidazole.

Reference Example 5

N-methyl-N-(1-(4-fluorobenzyl)benzimidazol-2-yl)-N'-methyl-N'-t-butoxycarbonyl-1,3-propylenediamine A solution comprising 1.0 g of N-methyl-N-(benzimidazol-2-yl)-N'-methyl-N'-t-butoxycarbonyl-1,3-propylenediamine, 540 mg of 4-fluorobenzyl chloride, 3 g of potassium carbonate and 20 ml of dimethylformamide, was reacted at room temperature overnight under a stirring condition. Further, it was reacted at a temperature of from 50 to 60° C. for 10 hours. Then, 50 ml of water was added thereto, and the mixture was extracted with ethyl acetate. The extract was dried over anhydrous sodium sulfate (30 ml×3), and then, the solvent was distilled off under reduced pressure. The obtained residue was purified by silica gel column chromatography (eluent: ethyl acetate) to obtain 1.4 g of the above identified compound as a colorless oily substance.

Reference Example 6

N-methyl-N-(1-(4-fluorobenzyl)benzimidazol-2-yl)-N'-methyl-N'-t-butoxycarbonyl-1,2-ethylenediamine In the same manner as in Reference Example 5, 1.3 g of the above identified compound was obtained as a pale yellow oily substance from 1.0 g of N-methyl-N-(benzimidazol-2-yl)-N'-methyl-N'-t-butoxycarbonyl-1,2-ethylenediamine.

Reference Example 7

N-methyl-N-(1-(4-fluorobenzyl)benzimidazol-2-yl) methyl -N'-methyl-N'-t-butoxycarbonyl-1,3-propylenediamine In the same manner as in Reference Example 5, 5.0 g of the above identified compound was obtained as a pale yellow oily substance from 6.5 g of N-methyl-N-(benzimidazol-2-yl)methyl-N'-methyl-N'-t-butoxycarbonyl-1,3-propylenediamine.

Reference Example 8

N-methyl-N-(1-(4-fluorobenzyl)benzimidazol-2-yl) methyl-N'-methyl-N'-t-butoxycarbonyl-1,2-ethylenediamine In the same manner as in Reference Example 5, 6.1 g of the above identified compound was obtained as a pale yellow oily substance from 6.0 g of N-methyl-N-(benzimidazol-2-yl)methyl-N'-methyl-N'-t-butoxycarbonyl-1,2-ethylenediamine.

Preparation Example 1

N-methyl-N-(1-(4-fluorobenzyl)benzimidazol-2-yl)-N'-methyl-N'-(3,5-bis(trifluoromethyl) benzylaminocarbonyl)-1,3-propylenediamine hydrochloride 2 ml of trifluoroacetic acid was added to 1.3 g of N-methyl-N-(1-(4-fluorobenzyl)benzimidazol-2-yl)-N'-methyl-N'-t-butoxycarbonyl-1,3-propylenediamine, and the mixture was stirred at room temperature for one hour. Then, 50 ml of water and 50 ml of chloroform were added thereto, and potassium carbonate was added thereto until the mixture became basic. The organic layer was taken and dried over anhydrous sodium sulfate. The solvent was distilled off under reduced pressure, to obtain 970 mg of a colorless oily substance. To 300 mg of this oily substance, 370 mg of phenyl N-(3,5-bis(trifluoromethyl)benzyl)carbamate was added, and the mixture was heated and stirred at 120° C. for two hours. After cooling, the obtained oily substance was purified by silica gel column chromatography (eluent: ethyl acetate/ethanol=9/1) to obtain 500 mg of a colorless oily substance. 250 mg of this oily substance was dissolved in 3 ml of ethanol, and 1 ml of 28% hydrochloric acid-ethanol was added thereto. The solvent was distilled off under reduced pressure, and the residue was crystallized from diethyl ether to obtain 280 mg of the above identified compound as colorless crystals. (m.p. 170.0–172.0° C.)

Preparation Example 2

N-methyl-N-(1-(4-fluorobenzyl)benzimidazol-2-yl)-N'-methyl-N'-(3,5-bis(trifluoromethyl) benzylaminocarbonyl)-1,2-ethylenediamine hydrochloride In the same manner as in Preparation Example 1, the above identified compound was obtained as colorless crystals from N-methyl-N-(1-(4-fluorobenzyl)benzimidazol-2-yl)-N'-methyl-N'-t-butoxycarbonyl-1,2-ethylenediamine. (m.p. 182.0–185.0° C.)

Preparation Example 3

N-methyl-N-(1-(4-fluorobenzyl)benzimidazol-2-yl) methyl-N'-methyl-N'-(3,5-bis(trifluoromethyl) benzylaminocarbonyl)-1,3-propylenediamine hydrochloride In the same manner as in Preparation Example 1, the above identified compound was obtained as a pale yellow oily substance from N-methyl-N-(1-(4-fluorobenzyl) benzimidazol-2-yl)methyl-N'-methyl-N'-t-butoxycarbonyl-1,3-propylenediamine.

Preparation Example 4

N-methyl-N-(1-(4-fluorobenzyl)benzimidazol-2-yl) methyl-N'-methyl-N'-(3,5-bis(trifluoromethyl) benzylaminocarbonyl)-1,2-ethylenediamine hydrochloride In the same manner as in Preparation Example 1, the above identified compound was obtained as colorless crystals from N-methyl-N-(1-(4-fluorobenzyl)benzimidazol-2-yl)methyl-N'-methyl-N'-t-butoxycarbonyl-1,2-ethylenediamine. (m.p. 144.0–145.0° C.)

Preparation Examples 5 to 13

In the same manner as in Preparation Example 1, the compounds shown in Table 2 were prepared in the form of their hydrochlorides.

TABLE 2

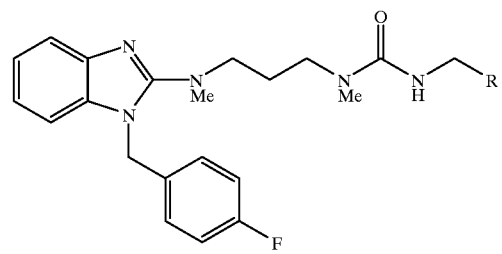

| Example No. | R | m.p. (° C.) |
|---|---|---|
| 5 | 2-MeO-phenyl | 197.0 |
| 6 | 2-Cl-phenyl | 211.0 |

TABLE 2-continued

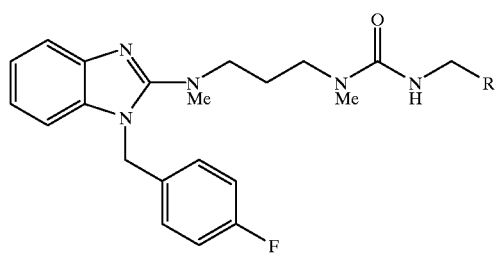

| Example No. | R | m.p. (° C.) |
|---|---|---|
| 7 | 2,3,4-(OMe)₃-phenyl | 184.0 |
| 8 | 3,5-(OMe)₂-phenyl | 139.0 |
| 9 | 4-F-phenyl | 175.0–178.0 |
| 10 | 3-OMe-phenyl | 138.0 |
| 11 | 3,5-Cl₂-phenyl | 156.0–159.0 |
| 12 | 4-OMe-phenyl | 176.0 |
| 13 | 4-Me-phenyl | 178.6 |

FORMULATION EXAMPLE 1
Tablets

| | |
|---|---|
| Compound of the present invention | 10 g |
| Lactose | 260 g |
| Microcrystalline cellulose | 600 g |
| Corn starch | 350 g |
| Hydroxypropyl cellulose | 100 g |
| CMC-Ca | 150 g |
| Magnesium stearate | 30 g |
| Total | 1,500 g |

The above ingredients were mixed by a conventional method and made into 10,000 sugar coated tablets containing 1 mg of the active ingredient per tablet.

FORMULATION EXAMPLE 2
Capsules

| | |
|---|---|
| Compound of the present invention | 10 g |
| Lactose | 440 g |
| Microcrystalline cellulose | 1,000 g |
| Magnesium stearate | 50 g |
| Total | 1,500 g |

The above ingredients were mixed by a conventional method and stuffed into gelatin capsules to obtain 10,000 capsules containing 1 mg of the active ingredient per capsule.

FORMULATION EXAMPLE 3
Soft elastic capsules

| | |
|---|---|
| Compound of the present invention | 10 g |
| PEG 400 | 479 g |
| Saturated fatty acid triglyceride | 1,500 g |
| Peppermint oil | 1 g |
| Polysorbate 80 | 10 g |
| Total | 2,000 g |

The above ingredients were mixed and then stuffed into No. 3 soft gelatin capsules by a conventional method to obtain 10,000 soft elastic capsules containing 1 mg of the active ingredient per capsule.

FORMULATION EXAMPLE 4
Ointment

| | |
|---|---|
| Compound of the present invention | 1.0 g |
| Liquid paraffin | 10.0 g |
| Cetanol | 20.0 g |
| White soft paraffin | 68.4 g |
| Ethyl paraben | 0.1 g |
| 1-menthol | 0.5 g |
| Total | 100.0 g |

The above ingredients were mixed by a conventional method to obtain 1% ointment.

| FORMULATION EXAMPLE: 5 Suppository | |
| --- | --- |
| Compound of the present invention | 1 g |
| Witepsol H15* | 478 g |
| Witepsol W35* | 520 g |
| Polysorbate 80 | 1 g |
| Total | 1,000 g |

*Tradename for a triglyceride type compound

The above ingredients were melti-mixed by a conventional method and poured into a suppository container, followed by cooling and solidification to obtain 1,000 pieces of a 1 g suppository containing 1 mg of the active ingredient.

| FORMULATION EXAMPLE 6 Injection | |
| --- | --- |
| Compound of the present invention | 1 mg |
| Distilled water for injection | 5 ml |

Whenever required, the injection is prepared by dissolving the compound in the distilled water.

TEST EXAMPLES

Inhibitory effect on substance P and histamine-induced contraction of the isolated guinea-pig ileum.

Compound

Test compounds were dissolved and diluted in 100% dimethylsulfoxide (DMSO). Substance P (SP, Peninsula Laboratories or Peptide Institute) and histamine dihydrochloride (Wako Pure Chemicals) were dissolved and diluted in distilled water. DMSO in organ bath did not exceed 0.25% v/v.

Methods

Male Hartley guinea-pigs (300–400 g) were killed by a blow to the head. The ileum was removed and the ileal strips (15–20 mm) were suspended under 0.5 g tension in a 20 ml organ bath containing a modified Tyrode solution maintained at 30° C. and aerated with 95% $O_2$+5% $CO_2$. Responses were recorded isotonically. Tissues were equilibrated for 15 min, and then the constant responses to histamine (1 μM) were obtained. Then substance P (0.01 μM) or histamine (0.1 μM)-induced contraction was obtained after 5 min incubation with or without the test compounds. Contractile responses to substance P or histamine with the test compound were expressed as a percentage of those without the test compound. $IC_{50}$ was the concentration of the test compound required to prevent 50% of the contractile response elicited by substance P or histamine. Compound Nos. of the tested compounds correspond to the numbers of Preparation Examples.

| Tested compounds | $IC_{50}$ (μM) | |
| --- | --- | --- |
| | Substance P | Histamine |
| 1 | 0.59 | 0.29 |
| 2 | 2.8 | 1.1 |
| 3 | 1.4 | 0.16 |
| 4 | 0.95 | 0.10 |

-continued

| Tested compounds | $IC_{50}$ (μM) | |
| --- | --- | --- |
| | Substance P | Histamine |
| 5 | 3.0 | 0.029 |
| 6 | 2.7 | 0.025 |
| 7 | 4.0 | 0.10 |
| 8 | 3.0 | 0.28 |
| 9 | 2.7 | 0.036 |
| 10 | 2.8 | 0.041 |
| 11 | 1.5 | 0.20 |
| 12 | 4.1 | 0.044 |
| 13 | 2.8 | 0.028 |

The compounds of the present invention exhibit antagonistic activities against substance P, and they are useful as anti-allergic agents.

What is claimed is:

1. A benzimidazole compound of the formula (I) or a salt thereof:

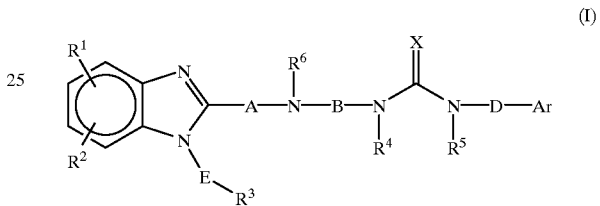

(I)

wherein A is a single bond or $C_{1-2}$ alkylene, which is optionally substituted by $C_{1-4}$ alkyl; $R^6$ is hydrogen, $C_{1-4}$ alkyl, which is optionally substituted by phenyl; B is $C_{2-3}$ alkylene, which is optionally substituted by $C_{1-4}$ alkyl; X is oxygen, sulfur, or $NR^7$, wherein $R^7$ is nitro, cyano or $C_{1-4}$ alkoxy; each of $R^1$ and $R^2$ which are independent of each other, is hydrogen, halogen, $C_{1-4}$ alkyl or $C_{1-4}$ alkoxy; E is $C_{1-2}$ alkylene, which is optionally substituted by $C_{1-4}$ alkyl; $R^3$ is phenyl, which is optionally substituted by halogen, $C_{1-4}$ alkyl or $C_{1-4}$ alkoxy, $C_{1-4}$ alkoxy or benzyloxy; each of $R^4$ and $R^5$ which are independent of each other, is hydrogen, $C_{1-4}$ alkyl, which is optionally substituted by phenyl; D is $C_{1-2}$ alkylene, which is optionally substituted by $C_{1-4}$ alkyl; and Ar is phenyl which is, optionally substituted by halogen, $C_{1-4}$ alkyl, $C_{1-4}$ alkoxy or trifluoromethyl.

2. The compound or the salt thereof of claim 1, wherein A is a single bond, $CH_2$, CHMe, $CH_2CH_2$ or $CH_2CHMe$; B is $CH_2CH_2$, $CH_2CHMe$, $CHMeCH_2$, CHMeCHMe, $CH_2CH_2CH_2$, $CHMeCH_2CH_2$, $CH_2CHMeCH_2$, $CH_2CH_2CHMe$, CHMeCHMeCH_2, $CHMeCH_2CHMe$, $CH_2CHMeCHMe$ or CHMeCHMeCHMe; D is $CH_2$, CHMe, $CH_2CH_2$ or $CH_2CHMe$; E is $CH_2$, CHMe, $CH_2CH_2$ or $CH_2CHMe$; Ar is phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl, 4-iodophenyl, 2-trifluoromethylphenyl, 3-trifluoromethylphenyl, 4-trifluoromethylphenyl, 2-methylphenyl, 3-methylphenyl, 4-methylphenyl, 2-methoxyphenyl, 3-methoxyphenyl, 4-methoxyphenyl, 2,3-difluorophenyl, 2,4-difluorophenyl, 2,5-difluorophenyl, 2,6-difluorophenyl, 3,4-difluorophenyl, 3,5-difluorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,3-dibromophenyl, 2,4-dibromophenyl, 2,5-dibromophenyl, 2,6-dibromophenyl, 3,4-dibromophenyl, 3,5-dibromophenyl, 2,3-diiodophenyl, 2,4-diiodophenyl, 2,5-diiodophenyl, 2,6-diiodophenyl, 3,4-diiodophenyl, 3,5-diiodophenyl, 2,3-bis(trifluoromethyl)phenyl, 2,4-bis(trifluoromethyl)phenyl, 2,5-bis(trifluoromethyl)phenyl, 2,6-bis(trifluoromethyl)phenyl, 3,4-bis(trifluoromethyl)phenyl, 3,5-bis(trifluoromethyl)phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl or 2-chloro-5-trifluoromethylphenyl, X is an oxygen atom, a sulfur atom, N—CN, N—NO$_2$, N—OMe, N—OE or N—OBu, each of $R^1$ and $R^2$ is a hydrogen atom, fluorine, chlorine, bromine, iodine, methyl, ethyl, n-propyl, i-propyl, c-propyl, n-butyl, i-butyl, s-butyl, t-butyl, c-butyl, methoxy, ethoxy, n-propoxy, i-propoxy, c-propoxy, n-butoxy, i-butoxy, s-butoxy, t-butoxy, or c-butoxy, $R^3$ is phenyl, 4-fluorophenyl, 4-chlorophenyl, methoxy, ethoxy or benzyloxy, each of $R^4$ and $R^5$ is a hydrogen atom, methyl, ethyl, n-propyl, i-propyl, c-propyl, n-butyl, i-butyl, s-butyl, t-butyl, c-butyl or benzyl, and $R^6$ is a hydrogen atom, methyl, ethyl, n-propyl, i-propyl, c-propyl, n-butyl, i-butyl, s-butyl, t-butyl, c-butyl or benzyl.

3. The compound or the salt thereof of claim 2, wherein X is oxygen.

4. The compound or the salt thereof of claim 3, wherein each of $R^1$ and $R^2$ is hydrogen.

5. The compound or the salt thereof of claim 2, wherein A is a single bond or CH$_2$; B is CH$_2$CH$_2$ or CH$_2$CH$_2$CH$_2$; D is CH$_2$, CHMe or CH$_2$CH$_2$; E is CH$_2$ or CH$_2$CH$_2$; Ar is phenyl, 2-chlorophenyl, 2-methoxyphenyl, 3,5-dimethylphenyl, 3,5-bis(trifluoromethyl)phenyl, 3,5-dimethoxyphenyl, 2,5-bis(trifluoromethyl)phenyl, 3,5-dimethoxyphenyl, 2,5-dichlorophenyl or 2-chloro-5-trifluoromethylphenyl; X is oxygen; each of $R^1$ and $R^2$ is hydrogen; $R^3$ is 4-fluorophenyl or ethoxy; each of $R^4$ and $R^5$ is hydrogen, methyl or benzyl; and $R^6$ is hydrogen, methyl or benzyl.

6. The compound or the salt thereof of claim 5, wherein E is CH$_2$; and $R^3$ is a 4-fluorophenyl group.

7. The compound or the salt thereof of claim 6, wherein Ar is 3,5-bis(trifluoromethyl)phenyl.

8. The compound or the salt thereof of claim 6, which is selected from the group consisting of N-methyl-N-(1-(4-fluorobenzyl)benzionidazol-2-yl)-N'-methyl-N-(3,5-bis(trifluoromethyl)benzylaminocarbonyl)-1,3-propylenediamine hydrochloride, N-methyl-N-(1-(4-fluorobenzyl)benzimidozol-2-yl)-N'-methyl-N'-(3,5-bis(trifluoromethyl)benzylaminocarbonyl)-1,2-ethylenedianine hydrochloride, N-methyl-N-(1-(4-fluorobenzyl)benzimidozol-2-yl)methyl-N'-methyl-N'-(3,5-bis(trifluoromethyl)benzylaminocarbonyl)-1,3-propylenediamine hydrochloride, and N-methyl-N(1-(4-fluorobenzyl)benzimidozol-2-yl)methyl-N'-methyl-N'-(3,5-bis(trifluoromethyl)benzylaminocarbonyl)-1,2-ethylinediamine hydrochloride.

9. The compound or the salt thereof claim 6, which has the formula:

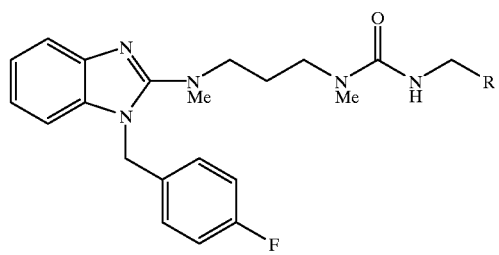

wherein R is selected from the group consisting of

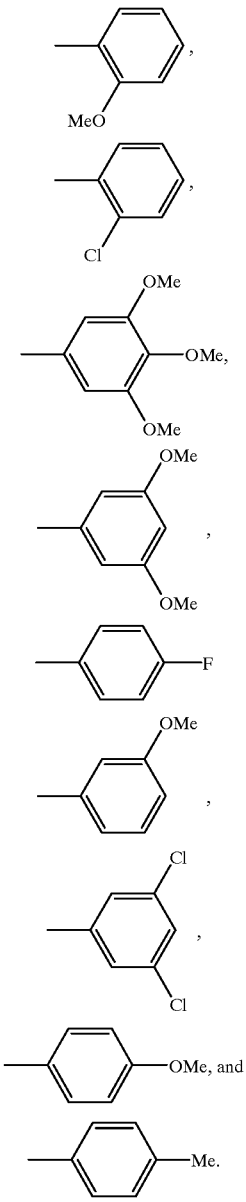

10. A pharmaceutical composition, which comprises an effective amount of the compound or the salt thereof of claim 2, and a pharmaceutically acceptable salt thereof.